United States Patent
Burg et al.

(10) Patent No.: US 6,528,481 B1
(45) Date of Patent: Mar. 4, 2003

(54) NG2/HM PROTEOGLYCAN-BINDING PEPTIDES THAT HOME TO ANGIOGENIC VASCULATURE AND RELATED METHODS

(75) Inventors: Michael A. Burg, San Diego; Renata Pasqualini; Wadih Arap, both of Solana Beach; Erkki Ruoslahti, Rancho Santa Fe; William B. Stallcup, Del Mar, all of CA (US)

(73) Assignee: The Burnam Institute, La Jolla, CA (US)

( * ) Notice: Subject to any disclaimer, the term of this patent is extended or adjusted under 35 U.S.C. 154(b) by 0 days.

(21) Appl. No.: 09/250,700

(22) Filed: Feb. 16, 1999

(51) Int. Cl.$^7$ .................... A01N 37/18; A01N 63/00; A61K 38/00; A61K 39/00; C07H 21/04

(52) U.S. Cl. .................... 514/2; 514/4; 514/15; 530/300; 530/305; 530/328; 530/395; 536/23.1; 536/23.5; 424/93.2; 424/185.1; 424/193.1

(58) Field of Search .................... 536/23.1, 23.5, 536/69.1; 435/320.1, 325, 455; 530/300, 305, 328, 395; 424/93.1, 93.2, 185.1, 193.1, 196.11, 277.1; 514/2, 4, 15

(56) References Cited

U.S. PATENT DOCUMENTS

| | | | |
|---|---|---|---|
| 5,536,814 A | 7/1996 | Ruoslahti et al. | 530/329 |
| 5,622,699 A | 4/1997 | Ruoslahti et al. | 424/93.6 |

FOREIGN PATENT DOCUMENTS

| | | | |
|---|---|---|---|
| WO | 95/14714 | 6/1995 | C07K/14/75 |
| WO | 97/10507 | 3/1997 | G01N/33/567 |
| WO | 97/13855 | 4/1997 | |
| WO | 97/19954 | 5/1997 | C07K/7/23 |
| WO | 97/39021 | 10/1997 | C07K/1/00 |
| WO | 98/10795 | 3/1998 | A61K/47/48 |

OTHER PUBLICATIONS

Molema et al, Biochem, Pharmacol. 55:1939–45, 1999.*
Kelloff et al, Eur. J. Cancer. 35(14):2031–2035, 1999.*
Gomez–Navarro et al, Eur. J. Cancer. 35(6);867–885, 1999.*
Burg et al Cancer Res. 59(12): 2869–74, 1999.*
Rajotte et al, J. Clin. Invest. 102(2): 430–347, 1998.*
Arap et al., "Cancer treatment by targeted drug delivery to tumor vasculature," *Science* 279:377–380 (1998).
Baillie et al., "Tumor Vasculature–A Potential Therapeutic Target" *British J. Cancer* 72:257–267 (1995).
Behm et al., "Human homologue of the rat chondroitin sulfate proteoglycan, NG2, detected by monoclonal antibody 7.1, identifies childhood acute lymphoblastic leukemias with t(4;11) (q21;q23) or t(11;19) (q23;13) and MLL gene rearragements," *Blood* 87:1134–1139 (1996).
Bicknell, "Vascular targeting and the inhibition of angiogenesis," *Annals of Oncology*, 5(Supp. 4): S45–S50 (1994).

Bigner, et al., "Phase I studies of treatment of malignant gliomas and neoplastic meningitis with $^{131}$I–radiolabeled monoclonal antibodies anti–tenascin 81C6 and anti–chondroitin sulfate proteoglycan Mel–14F(ab')$_2$—a preliminary report," *J. Neuro–Oncol.*, 24:109–122 (1995).
Bumol, et al., "Monoclonal antibody and an antibody–toxin conjugate to a cell surface proteoglycan of melanoma cells suppress in vivo tumor growth," *Proc. Natl. Acad. Sci. USA*, 80:529–533 (1983).
Burg, et al., "Binding of the NG2 proteoglycan to type VI collagen and other extracellular matrix molecules," *J. Biol. Chem.*, 271:26110–26116 (1996).
Burg, et al., "A central segment of the NG2 proteoglycan is critical for the ability of glioma cells to bind and migrate toward type VI collagen," *Exp. Cell Res.*, 235:254–264 (1997).
Burg, et al., "Expression of the NG2 proteoglycan enhances the growth and metastatic properties of melanoma cells," *J. Cell. Physiol.*, 177:299–312 (1998).
Burrows and Thorpe, "Vascular targeting—A new approach to the therapy of solid tumors" *Pharmac. Ther.* 64:155–174 (1994).
Dvorak et al., "Structure of solid tumors and their vasculature: implications for therapy with monoclonal antibodies" *Cancer Cells* 3:77–85 (1991).
Folkman, "Addressing tumor blood vessels," *Nature Biotechnology*, 15:510 (1997).
Grako and Stallcup, "Participation of the NG2 proteoglycan in rat aortic smooth muscle cell responses to platelet–derived growth factor," *Exp. Cell Res.*, 221:231–240 (1995).
Hanahan, "Signaling vascular morphogenesis and maintenance," *Science*, 277:48–50 (1997).

(List continued on next page.)

*Primary Examiner*—Scott D. Priebe
*Assistant Examiner*—Sumesh Kaushal
(74) *Attorney, Agent, or Firm*—Campbell & Flores LLP

(57) ABSTRACT

The present invention provides angiogenic vasculature homing molecules that bind to NG2/HM proteoglycan, including, for example, a peptide comprising the amino acid sequence TAASGVRSMH (SEQ ID NO:1) or LTLRWVGLMS (SEQ ID NO:2). The invention also provides conjugates comprising an angiogenic vasculature homing molecule linked to a moiety such as a drug, a cytotoxic agent, a chemotherapeutic agent, or a detectable agent. The invention additionally provides a method of targeting angiogenic vasculature in a tumor in vivo by contacting the angiogenic vasculature with an angiogenic vasculature homing molecule that selectively homes to a NG2/HM proteoglycan, wherein the angiogenic vasculature homing molecule is not an antibody. The invention additionally provides a method of inhibiting angiogenesis in a tumor of a subject by administering to the subject a conjugate comprising a moiety linked to an angiogenic vasculature homing molecule that selectively binds a NG2/HM proteoglycan, wherein the angiogenic vasculature homing molecule is not an antibody.

33 Claims, 4 Drawing Sheets

OTHER PUBLICATIONS

Harper and Reisfeld, "Cell–associated proteoglycans in human malignant melanoma," *Biology of Proteoglycans* Acad. Press pp. 345–366 (1987).

Harper and Reisfeld, "Inhibition of anchorage–independent growth of human melanoma cells by a monclonal antibody to a chondroitin sulfate proteoglycan," *J. Natl. Cancer Inst.* 71:259–263 (1983).

Iida, et al., "Spreading and focal contact formation of human melanoma cells in response to the stimulation of both NG2 $\alpha_4\beta_1$ integrin," *Cancer Res.*, 55:2177–2185 (1995).

Kerbel, "Inhibition of Tumor Angiogenesis as a Strategy to Circumvent Aquired Resistance to Anti–Cancer Therapeutic Agents," *BioEssays*, 13(1):31–36 (1991).

Koivunen et al., "Phage libraries displaying cyclic peptides with different ring sizes: ligand specifications of the RGD–directed integrins," *Biotechnology* 13 (3):265–270 (1995).

Koivunen et al., "Selection of peptides binding to the $\alpha5\beta1$ integrin from phage display library," *J. Biol. Chem.* 268:20205–20210 (1993).

Leger, et al., "The chondroitin sulfate proteoglycan NG2 is a tumor specific antigen on the chemically induced rat chondrosarcoma HSN," *Int. J. Cancer*, 58:700–705 (1994).

Martiny–Baron and Marmé, "VEGF–mediated tumor angiogenesis: a new target for cancer therapy" *Current Opinion Biotechnol* 6:675–680 (1995).

Nagy et al., "Synthesis and biological evaluation of cytotoxic analogs of somatostatin containing doxorubicin or its intensely potent derivative, 2–pyrrolinodoxorubicin," *Proc. Natl. Acad. Sci. USA* 95:1794–1799 (1998).

Nagy et al., "Cytotoxic analogs of luteinizing hormone–releasing hormone containing doxorubicin or 2–pyrrolinodoxorubiciin, a derivative 500–1000 times more potent," *Proc. Natl. Acad. Sci. USA*, 7269–7273 (1996).

Nishiyama and Stallcup, "Expression of NG2 Proteoglycan Causes Retention of Type VI Collagen on the Cell Surface," *Mol. Biol.Cell*, 4:1097–1108 (1993).

Nishiyama, et al., "Interaction between NG2 proteoglycan and PDGF $\alpha$ receptor is required for optimal response to PDGF," *J. Neurosci. Res.*, 43:315–330 (1996).

Nishiyama et al., "The primary structure of NG2, a novel membrane–spanning proteoglycan," *J. Cell Biol.* 114:359–371 (1991).

Pasqualini et al., "$\alpha$v Integrins as receptors for tumor targeting by circulating ligands," *Nature Biotechnology*l, 15:542–546 (1997).

Pasqualini and Ruoslahti, "Organ Targeting in vivo Using Phage Display Peptide Libraries" *Nature* 380:364–366 (1996).

Pasqualini et al., "A Peptide Isolated from Phage Display Libraries Is a Structural and Functional Mimic of an RGD–binding Site on Integrins," *J. Cell Biol.* 130:1189–1196 (1995).

Pluschke et al., "Molecular cloning of a human melanoma–associated chondroitin sulfate proteoglycan," *Proc. Natl. Acad. Sci. USA*, 93:9710–9715 (1996).

Rajotte et al., "Molecular Hetergeneity of the Vascular Endothelium Revealed by In Vivo Phage Display," *J. Clin. Invest.* 102:430–437 (1998).

Rak et al., "Consequences of angiogenesis for tumor progression, metastasis and cancer therapy," *Anti–Cancer Drugs*, 6:3–18 (1995).

Real et al., "Surface antigens of melanomas and melanocytes defined by mouse monoclonal antibodies: specificity, analysis, and comparison of antigen expression in cultured cells and tissues," *Cancer Res.*, 45:4401–4411 (1995).

Schlingemann et al., "Differential expression of markers for endothelial cells, pericytes, and basal lamina in the microvasculature of tumors and granulation tissue," *Amer. J. Path.* 138:1335–1347 (1991).

Schlingemann, et al., "Expression of the high molecular weight melanoma–associated antigen by pericytes during angiogenesis in tumors and in healing wounds," *Amer. J. Path*, 136:1393–1405 (1990).

Schrappe, et al., "Correlation of chondroitin sulfate proteoglycan expression on proliferating brain capillary endothelial cells with the malignant phenotype of astroglial cells," *Cancer Res.* 51:4986–4993 (1991).

Spitler et al., "Therapy of patients with malignant melanoma using a monoclonal anti–melanoma antibody–ricin immunotoxin," *Cancer Res.* 47:1717–1723 (1987).

Tillet et al., "The membrane–spanning proteoglycan NG2 binds to collagen V and VI through the central non–globular domain of its core protein," *J. Biol. Chem.* 272:10769–10776 (1997).

Yang and Reisfeld, "Doxorubicin conjugated with a monoclonal antibody directed to a human melanoma–associated proteoglycan suppresses the growth of established tumor xenografts in nude mice," *Proc. Natl. Acad. Sci. USA* 85:1189–1193 (1988).

Bicknell, "Vasculature targeting and the inhibition of angiogenesis," *Annals of Oncology*, 5:S45–S50 (1994).

Rihova, "Targeting of Drugs to Cell Surface Receptors," *Critical Reviews in Biotechnology*, 17:149–169 (1997).

* cited by examiner

NG2/HM PROTEOGLYCAN-BINDING PEPTIDES THAT HOME TO ANGIOGENIC VASCULATURE AND RELATED METHODS

This invention was made with government support under grant numbers RO1CA74238, RO1NS21990, RO1NS32767 and F32CA72220 awarded by the National Institutes of Health and under grant number CA30199 awarded by the National Cancer Institute. The government has certain rights in the invention.

BACKGROUND OF THE INVENTION

1. Field of the Invention

The present invention relates generally to the fields of cancer biology and drug delivery and, more specifically, to peptides that selectively home to angiogenic vasculature, particularly in a tumor, to compositions comprising an agent such as a therapeutic agent conjugated to such angiogenic vasculature homing molecules, and to methods of using such molecules to target an agent to angiogenic vasculature.

2. Background Information

Continuous developments over the past quarter century have resulted in substantial improvements in the ability of a physician to diagnose a cancer in a patient. For example, antibody based assays such as that for prostate specific antigen now allow early diagnosis of cancers such as prostate cancer. More recently, methods of genetic screening are becoming available to identify persons that may be particularly susceptible to developing a cancer. Genetic screening methods are based on the identification of one or more mutations in a gene that correlates with the development of a cancer. For example, the identification of genes such as BRCA1 and BRCA2 allowed the further identification of mutations in these genes that, in some cases, can correlate with susceptibility to developing breast cancer.

Unfortunately, methods for treating cancer have not kept pace with those for diagnosing the disease. Thus, while the death rate from various cancers has decreased due to the ability of a physician to detect the disease at an earlier stage, the ability to treat patients presenting with more advanced disease has progressed only minimally.

A major hurdle to advances in treating cancer is the relative lack of agents that can selectively target the cancer, while sparing normal tissue. For example, radiation therapy and surgery, which generally are localized treatments, can cause substantial damage to normal tissue in the treatment field, resulting in scarring and, in severe cases, loss of function of the normal tissue. Chemotherapy, in comparison, which generally is administered systemically, can cause substantial damage to organs such as bone marrow, mucosae, skin and the small intestine, which undergo rapid cell turnover and continuous cell division. As a result, undesirable side effects such as nausea, loss of hair and drop in blood cell count occur as a result of systemically treating a cancer patient with chemotherapeutic agents. Such undesirable side effects often limit the amount of a treatment that can be administered. Thus, cancer remains a leading cause of patient morbidity and death.

Efforts have been made to increase the target specificity of various drugs. For example, where a unique cell surface marker is expressed by a population of cells making up a tumor, an antibody can be raised against the unique marker and a drug can be linked to the antibody. Upon administration of the drug/antibody complex to the patient, the binding of the antibody to the marker results in the delivery of a relatively high concentration of the drug to the tumor. Similar methods can be used where a particular cancer cell or the supporting cell or matrix expresses a unique cell surface receptor or a ligand for a particular receptor. In these cases, the drug can be linked to the specific ligand or to the receptor, respectively, thus providing a means to deliver a relatively high concentration of the drug to the tumor.

Tumors are characterized, in part, by a relatively high level of active angiogenesis, resulting in the continual formation of new blood vessels to support the growing tumor. Such angiogenic blood vessels are distinguishable from mature vasculature. One of the distinguishing features of angiogenic vasculature is that unique endothelial cell surface markers are expressed. Thus, the blood vessels in a tumor provide a potential target for directing a chemotherapeutic agent to the tumor, thereby reducing the likelihood that the agent will kill sensitive normal tissues.

Although antibody-based therapies have been effective at treating certain types of cancer, antibody-based therapies also have limitations, mostly due to poor tissue penetration and unwanted immune response. Therefore, the identification of small molecules such as peptides capable of targeting cells within tumor vasculature or stroma can be useful in alleviating many of the problems associated with antibody-based targeting strategies.

While linking a drug to a molecule that homes to a tumor can provide significant advantages for treatment over the use of a drug, alone, use of this method is severely limited by the scarcity of useful cell surface markers expressed in a tumor. Thus, a need exists to identify molecules that can selectively home to a tumor, particularly to the vasculature supporting the tumor. The present invention satisfies this need and provides related advantages as well.

SUMMARY OF THE INVENTION

The present invention provides angiogenic vasculature homing molecules that bind to NG2/HM proteoglycan. Angiogenic vasculature homing molecules of the invention include, for example, a peptide comprising the amino acid sequence TAASGVRSMH (SEQ ID NO:1) or LTLRWVGLMS (SEQ ID NO:2). The invention also provides conjugates comprising an angiogenic vasculature homing molecule linked to a moiety such as a drug, a cytotoxic agent, a chemotherapeutic agent, or a detectable agent.

The invention additionally provides a method of targeting angiogenic vasculature in a tumor in vivo. The method includes the steps of contacting the angiogenic vasculature with an angiogenic vasculature homing molecule that selectively homes to a NG2/HM proteoglycan, wherein the angiogenic vasculature homing molecule is not an antibody. The method can be used to target a drug, a cytotoxic agent, or a chemotherapeutic agent to angiogenic vasculature, or can be used to target a detectable agent for imaging a tumor, tissue or organ associated with angiogenic vasculature.

The invention further provides a method of inhibiting angiogenesis in a tumor of a subject. The method includes the steps of administering to the subject a conjugate comprising a moiety linked to an angiogenic vasculature homing molecule that selectively binds a NG2/HM proteoglycan, wherein the angiogenic vasculature homing molecule is not an antibody. The method can be used to inhibit angiogenesis by targeting an angiogenic vasculature homing molecule linked to a therapeutic moiety to the angiogenic vasculature of a tumor.

DETAILED DESCRIPTION OF THE INVENTION

Figure 1:
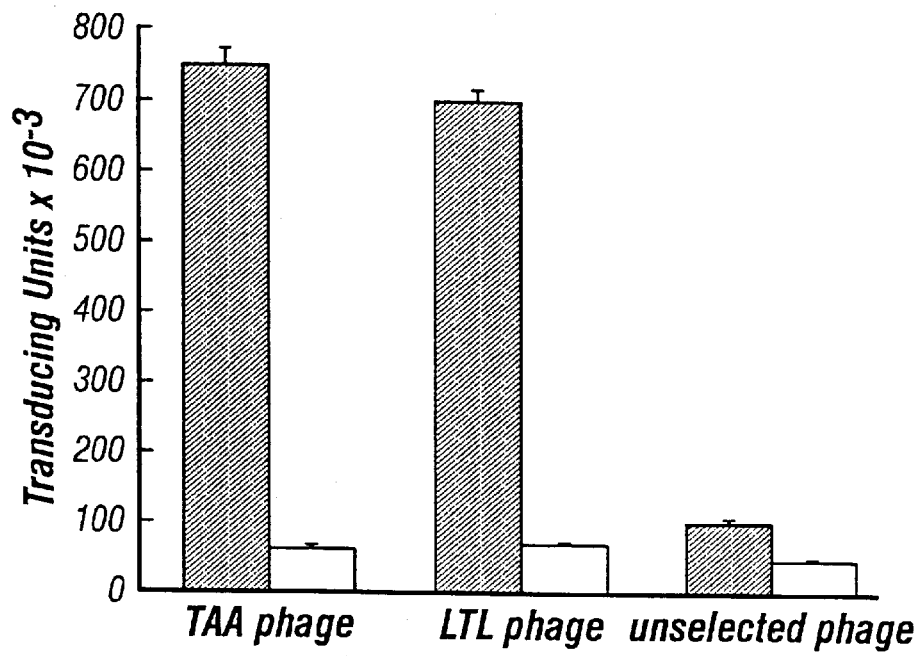
FIG. 1 shows attachment of phage expressing peptides to NG2. Purified TAASGVRSMH-phage (TAA phage) and LTLRWVGLMS-phage (LTL phage), or an unselected decapeptide phage library mix (unselected phage), were incubated on NG2Δ3-coated (solid bar) or BSA-coated (gray bar) microtiter wells, and bound phage were quantified.

The present invention relates to the identification of angiogenic vasculature homing molecules that bind to NG2/HM proteoglycan. As disclosed herein, various peptides were identified that bind to NG2/HM proteoglycan. In particular, phage expressing the peptides TAASGVRSMH (SEQ ID NO:1) and LTLRWVGLMS (SEQ ID NO:2) specifically bind to NG2/HM proteoglycan. Furthermore, these peptides that bind to NG2/HM proteoglycan homed to the angiogenic vasculature of tumors in mice bearing mouse melanomas.

The invention provides angiogenic vasculature homing peptides that bind to NG2/HM proteoglycan. For example, the invention provides an angiogenic vasculature homing peptide comprising the amino acid sequence TAASGVRSMH (SEQ ID NO:1) or LTLRWVGLMS (SEQ ID NO:2).

As disclosed herein, a phage library expressing decapeptides was screened for binding to rat NG2, and various peptides were identified having NG2 binding activity (see Table 1, Example 1). Two peptides, TAASGVRSMH (SEQ ID NO:1) and LTLRWVGLMS (SEQ ID NO:2), were consistently found in later rounds of in vitro screening. Although the sequences are distinct, the peptides do share small areas of similarity, for example, VR versus LR, SM versus MS, and ASG versus LTL in TAASGVRSMH (SEQ ID NO:1) and LTLRWVGLMS (SEQ ID NO:2), respectively. Since these distinct peptides appear to bind at the same or overlapping sites on NG2, the peptides could function as mimotopes of each other at regions of similarity (see Examples II and III). These peptides showed no similarity to known ligands for NG2/HM proteoglycan (Burg et al., *J. Cell. Physiol.* 177:299–312 (1998); Burg et al., *J. Biol. Chem.* 271:26110–26116 (1996); Tillet et al., *J. Biol. Chem.* 272:10769–10776 (1997)).

It is understood that, since NG2 is associated with angiogenic vasculature, any of the peptides of Table 1 can be used as an angiogenic vasculature homing peptide. Therefore, the invention also provides an angiogenic vasculature homing peptide selected from the group consisting of GGGTRAGMKY (SEQ ID NO:3); WGKIEDPLRA (SEQ ID NO:4); AGQTLTASGD (SEQ ID NO:5); DLLAVSWLRA (SEQ ID NO:6); SAERGVVAMS (SEQ ID NO:7); AIHSELMWVS (SEQ ID NO:8); FWTERAGWAY (SEQ ID NO:9); MVWSKGPLFL (SEQ ID NO:10); AGTRMSWEVL (SEQ ID NO:11); VSRSSRWGSI (SEQ ID NO:12); DAHVLVPRTP (SEQ ID NO:13); AQGIVLQLAL (SEQ ID NO:14); and LSPLLSPATA (SEQ ID NO:15). Furthermore, the peptide CLSGSLSC (SEQ ID NO:16) was also found to bind to NG2 and therefore can function as a peptide angiogenic vasculature homing molecule that homes to NG2/HM proteoglycan.

Angiogenic vasculature homing molecules that are peptides can consist of about 8 amino acids or less, about 9 amino acids or less, about 10 amino acids or less, but can also consist of about 12 amino acids or less, about 15 amino acids or less, about 18 amino acids or less, about 20 amino acids or less, about 25 amino acids or less, about 30 amino acids or less, about 35 amino acids or less, about 40 amino acids or less, about 45 amino acids or less, or about 50 amino acids or less.

The invention also provides a method of targeting angiogenic vasculature in a tumor in vivo by contacting the angiogenic vasculature with an angiogenic vasculature homing molecule that selectively binds a NG2/HM proteoglycan, wherein the angiogenic vasculature homing molecule is not an antibody.

As used herein, the term "NG2/human melanoma proteoglycan" or "NG2/HM proteoglycan" refers to the mammalian proteoglycan corresponding to the rat NG2 proteoglycan and the human melanoma proteoglycan, which is also known as the high molecular weight melanoma associated antigen. NG2/HM proteoglycan is a chondroitin sulfate proteoglycan. The sequence of rat and human NG2/HM proteoglycan has been previously described (Nishiyama et al., *J. Cell Biol.* 114:359–371 (1991a; Pluschke et al., *Proc. Natl. Acad. Sci. USA* 93:9710–9715 (1996), each of which is incorporated herein by reference).

The rat proteoglycan NG2 and its homolog, the human melanoma proteoglycan (HMP) is a developmentally regulated, membrane-spanning chondroitin sulfate proteoglycan expressed primarily by glial, muscle and cartilage progenitor cells. Upon maturation of these cells, NG2/HM proteoglycan expression is downregulated in these cell types. In adults, the expression of NG2/HM proteoglycan is restricted to tumor cells and angiogenic tumor vasculature. NG2/HM proteoglycan is widely expressed by several different tumors including glioblastomas, chondrosarcomas, melanomas, and some leukemias (Nishiyama et al., supra, 1991a; Pluschke et al., *Proc. Natl. Acad. Sci. USA* 93:9710–9715 (1996); Behm et al., *Blood* 87:1134–1139 (1996); Real et al., *Cancer Res.* 45:4401–4411 (1985); Schrappe et al., *Cancer Res.* 51:4986–4993 (1991); Leger et al., *Int. J. Cancer* 58:700–705 (1994)). Previous studies have shown that NG2/HM proteoglycan expression increases the proliferative capacity of melanoma cells (Bumol et al., *Proc. Natl. Acad. Sci. USA* 80:529–533 (1983); Harper and Reisfeld, *J. Natl. Cancer Inst.* 71:259–263 (1983); Harper and Reisfeld, in *Biology of Proteoglycans*, Wight and Mecham, eds., Academic Press, pp.345–366 (1987); Burg et al., *J. Cell Physiol.* 177:299–312 (1998)). Moreover, antibodies against NG2/HM proteoglycan inhibit melanoma growth both in vitro and in vivo (Bumol et al., supra, 1983; Harper and Reisfeld, supra, 1983; Harper and Reisfeld, supra, 1987).

Transfection of NG2 into NG2-negative B16F1 and B16F10mouse melanoma cell lines was found to increase both the proliferative capacity of these cells in vitro and tumor size in vivo (Burg et al., supra, 1998). NG2 expression also increased lung colonization for both B16F1 and B16F10 cells in experimental metastasis studies. While the specific mechanism by which NG2 enhances the proliferative and metastatic properties of these cells has not been elucidated, association of NG2 with known extracellular matrix ligands such as type VI collagen or cellular ligands such as CD44 and $\alpha_4\beta_1$ integrin, and its ability to enhance cellular responses to at least one growth factor, PDGF-AA, appear to be important in the proliferative and metastatic properties associated with NG2 (Burg et al., supra, 1998; Nishiyama and Stallcup, *Mol. Biol. Cell* 4:1097–1108 (1993); Burg et al., *J. Biol. Chem.* 271:26110–26116 (1996); Burg et al., *Exp. Cell Res.* 235:254–264 (1997); Tillet et al., *J. Biol. Chem.* 272:10769–10776 (1997); Iida et al., *Cancer Res.* 55:2177–2185 (1995); Grako and Stallcup, *Exp. Cell Res.* 221:231–240 (1995); Nishiyama et al., *J. Neurosci. Res.* 43:315–330 (1996)).

NG2/HM proteoglycan is also widely expressed by angiogenic blood vessels. This is true not only for the expanding vasculature of normally developing tissues but also for the neovasculature found in tumor stroma and in granulation tissue of healing wounds (Schrappe et al., supra 1991; Grako and Stallcup, supra, 1995; Schlingemann et al., *Amer. J. Path.* 136:1393–1405 (1990); Schlingemann et al., *Amer. J. Path.* 138:1335–1347 (1991)). In contrast, NG2/HM proteoglycan is not detectable in normal quiescent vasculature. Immunohistochemical studies have suggested that NG2/HM proteoglycan expression in neovasculature is limited to the neovascular pericytes (Schlingemann et al., supra, 1990; Schlingemann et al., supra, 1991)). However, NG2/HM proteoglycan expression by endothelial cells in developing brain capillaries has also been reported (Schrappe et al., supra, 1991; Grako and Stallcup, supra, 1995). Pericytes are intimately associated with endothelial cells in developing vasculature and are thought to affect angiogenesis by regulating endothelial cell proliferation, directing microvessel outgrowth, and stabilizing capillary walls (Sims, *Tiss. Cell,* 18:153–174 (1986); Hirschi and D'Amore, in *Regulation of Angiogenesis*, Goldberg and Rosen, eds., Birkhauser Verlag, Basel, pp. 419–428 (1997); Lindahl and Betzholtz, *Curr. Op. Nephrol. Hypert.* 7:21–26 (1998); Lindahl et al., *Science* 277:242–245 (1997)).

The selective expression of NG2/HM proteoglycan in tumor cells and tumor vasculature makes this molecule an attractive target for anti-cancer therapies. An anti-NG2/HM proteoglycan monoclonal antibody (mAb)-doxorubicin conjugate was shown to suppress malignant melanoma growth in a nude mouse model (Yang and Reisfeld, *Proc. Natl. Acad. Sci. USA* 85:1189–1193 (1988)). Additionally, anti-NG2/HM proteoglycan mAb-toxin and $^{131}$I-radiolabeled conjugates have been shown to have some therapeutic value for patients with malignant melanoma (Spitler et al., *Cancer Res.* 47:1717–1723 (1987); Bigner et al., *J. Neuro-Oncol.* 24:109–122 (1995)).

Although antibody-based therapies have been effective at treating certain types of cancer, antibody-based therapies also have limitations, mostly due to poor tissue penetration and unwanted immune response (Baillie et al., *Br. J. Cancer* 72:257–267 (1995); Burrows and Thorpe, *Proc. Natl. Acad. Sci. USA* 90:8996–9000 (1993); Shockley et al., *Ann. N.Y. Acad. Sci.* 618:367–382 (1991); Dvorak et al., *Cancer Cells* 3:77–85 (1991); Molema et al., *Pharmaceutical Res.* 14:2–10 (1997); Jain, *Microcirculation* 4:3–23 (1997)). Therefore, the identification of small molecules such as peptides capable of targeting cells within tumor vasculature or stroma can be useful in alleviating many of the problems associated with antibody-based targeting strategies (Folkman, in *Cancer: Principles and Practice of Oncology*, 5th ed., DeVita et al., eds., Lippincott-Raven, Philadelphia, pp. 3075–3085 (1997a); Arap et al., *Curr. Opin. Oncol.* 10:560–565 (1998); Jain, supra, 1997)). Thus, the angiogenic vasculature homing molecules of the invention, which bind NG2/HM proteoglycan, are particularly useful for targeting a drug or toxin to angiogenic vasculature of a tumor.

A functional fragment of a NG2/HM proteoglycan also can be useful in the methods of the invention, for example, for identifying homing molecules that home to angiogenic vasculature such as in a tumor. As used herein, the term "functional fragment," when used in reference to a NG2/HM proteoglycan, refers to a portion of a NG2/HM proteoglycan that retains some or all specific binding activity to a homing molecule. Such a functional fragment can be, for example, the extracellular domain of a NG2/HM proteoglycan or an epitope specifically reactive with an antibody. A functional fragment of a NG2/HM proteoglycan useful in identifying a homing molecule can be, for example, the N-terminal two-thirds of the extracellular domain (see Example I).

As used herein, the term "specific binding" means binding that is measurably different from a non-specific interaction. Specific binding can be measured, for example, by determining binding of a molecule compared to binding of a control molecule, which generally is a molecule of similar structure that does not have binding activity, for example, a peptide of similar size that lacks binding activity. In this case, specific binding is indicated if the molecule has measurably higher affinity for the NG2/HM proteoglycan than the control molecule. Specificity of binding can be determined, for example, by competition with a control molecule that is known to bind to a target. For example, specific binding of a molecule that binds a NG2/HM proteoglycan can be demonstrated by competing for binding with the same molecule. In this case, specific binding is indicated if the binding of a molecule is competitively inhibited by itself.

The term "specific binding," as used herein, includes both low and high affinity specific binding. Specific binding can be exhibited, for example, by a low affinity homing molecule having a Kd of at least about $10^{-4}$ M. For example, if the receptor for a homing molecule has more than one binding site, a homing molecule having low affinity can be useful for targeting angiogenic vasculature. Specific binding also can be exhibited by a high affinity homing molecule, for example, a homing molecule having a Kd of at least about of $10^{-7}$ M, at least about $10^{-8}$ M, at least about $10^{-9}$ M, at least about $10^{-10}$ M, or can have a Kd of at least about $10^{-11}$ M or $10^{-12}$ M or greater. Both low and high affinity homing molecules are useful for targeting angiogenic vasculature.

The invention provides a method of identifying a homing molecule that homes to NG2/HM proteoglycan and, due to the association of NG2/HM proteoglycan with angiogenic vasculature, to angiogenic vasculature. The method includes the steps of contacting a substantially purified NG2/HM proteoglycan with one or more molecules, and determining specific binding of a molecule to the NG2/HM proteoglycan, wherein the presence of specific binding identifies the molecule as a homing molecule that homes to angiogenic vasculature. The method can further comprise the steps of administering an NG2/HM proteoglycan binding molecule in vivo; and determining binding of the NG2/HM proteoglycan molecule to angiogenic vasculature.

The vasculature within a tumor generally undergoes active angiogenesis, resulting in the continual formation of new blood vessels to support the growing tumor. Such angiogenic blood vessels are distinguishable from mature vasculature in that angiogenic vasculature expresses unique endothelial cell surface markers, including the $\alpha_v\beta_3$ integrin (Brooks, *Cell* 79:1157–1164 (1994), which is incorporated herein by reference); WO 95/14714, Int. Filing Date Nov. 22, 1994) and receptors for angiogenic growth factors (Mustonen and Alitalo, *J. Cell Biol.* 129:895–898 (1995); Lappi, *Semin. Cancer Biol.* 6:279–288 (1995)). Moreover, tumor vasculature is histologically distinguishable from blood vessels in general in that tumor vasculature is fenestrated (Folkman, *Nature Med.* 1:27–31 (1995); Rak et al., *Anticancer Drugs* 6:3–18 (1995)). Thus, angiogenic vasculature is an attractive target for identifying a homing molecule, particularly for targeting a tumor. Such an angiogenic vasculature homing molecule can be useful for directing an agent such as a chemotherapeutic drug to a tumor, while reducing the likelyhood the agent will have a toxic effect on normal, healthy organs or tissues. Moreover, a molecule that homes selectively to angiogenic vasculature also may have use in targeting other types of neovasculature such as that present in inflammatory, regenerating or wounded tissues. The term "homing molecule that homes to angiogenic vasculature" means a molecule that can bind specifically to a target molecule expressed in angiogenic vasculature. It is understood that an angiogenic homing molecule can be a tumor homing molecule if the angiogenic vasculature is associated with a tumor.

The invention provides a method for directly identifying molecules that can selectively home to NG2/HM proteoglycan and to angiogenic vasculature by screening for molecules that bind to NG2/HM proteoglycan. As used herein, the term "home" or "selectively home" means that a particular molecule binds relatively specifically to a target molecule present in angiogenic vasculature following administration to a subject. In general, selective homing is characterized, in part, by detecting at least a two-fold (2×) greater specific binding of the molecule to angiogenic vasculature as compared to a control organ or tissue. The invention additionally provides homing molecules and angiogenic vasculature homing molecules that home to NG2/HM proteoglycan.

A homing molecule can bind to angiogenic vasculature in a tumor or in non-tumor tissue. A homing molecule that binds to both tumor and non-tumor angiogenic vasculature also can exhibit preferential binding to tumor or non-tumor tissues. Thus, the invention provides methods for identifying homing molecules that bind to angiogenic vasculature in non-tumor tissue as well as homing molecules that home to angiogenic vasculature of a tumor.

A homing molecule that homes to angiogenic vasculature is identified by screening one or more molecules, for example, a library of molecules. As used herein, the term "library" means a collection of molecules. A library can contain a few or a large number of different molecules, varying from about ten molecules to several billion molecules or more. If desired, a molecule can be linked to a tag, which can facilitate recovery or identification of the molecule. As disclosed herein, a homing molecule that homes to angiogenic vasculature can be identified by in vitro screening against a substantially purified NG2/HM proteoglycan (Example I).

As used herein, the term "molecule" is used broadly to mean an organic chemical such as a drug; a nucleic acid molecule such as an RNA, a cDNA or an oligonucleotide; a peptide, including a variant or modified peptide or peptide-like molecules, referred to herein as peptidomimetics, which mimic the activity of a peptide; or a protein such as an antibody or a growth factor receptor or a fragment thereof such as an Fv, single chain Fv(scFv), Fd or Fab fragment of an antibody, which contains a binding domain. For convenience, the term "peptide" is used broadly herein to mean peptides, proteins, fragments of proteins and the like, which can have, for example, a cyclic or linear conformation. A molecule also can be a non-naturally occurring molecule, which does not occur in nature, but is produced as a result of in vitro methods, or can be a naturally occurring molecule such as a protein or fragment thereof expressed from a cDNA library.

A molecule to be screened against a substantially purified NG2/HM proteoglycan according to a method of the invention can be a "peptidomimetic," which is used broadly to mean a peptide-like molecule that has the binding activity of an angiogenic vasculature homing peptide. Thus, peptidomimetics, including chemically modified peptides, peptide-like molecules containing non-naturally occurring amino acids, peptoids and the like, and, in particular, peptidomimetics of a peptide that binds a NG2/HM proteoglycan, can be screened for the ability to specifically bind a NG2/HM proteoglycan, and thus, for activity in homing to angiogenic vasculature (see, for example, "Burger's Medicinal Chemistry and Drug Discovery" 5th ed., vols. 1 to 3 (ed. M. E. Wolff; Wiley Interscience 1995), which is incorporated herein by reference). Peptidomimetics provide various advantages over a peptide, for example, increased stability during passage through the digestive tract and, therefore, are advantageously used for oral administration.

Collections or libraries of peptidomimetics are well known in the art, for example, databases that contain libraries of potential peptidomimetics. For example, the Cambridge Structural Database contains a collection of greater than 300,000 compounds that have known crystal structures (Allen et al., *Acta Crystallogr*. Section B, 35:2331 (1979)). This structural depository is continually updated as new crystal structures are determined and can be screened for compounds having suitable shapes, for example, the same shape as an angiogenic vasculature homing molecule such as a NG2/HM proteoglycan binding peptide, as well as potential geometrical and chemical complementarity to a NG2/HM proteoglycan bound by an angiogenic vasculature homing peptide. Where no crystal structure is available for an angiogenic vasculature homing peptide or a NG2/HM proteoglycan, which binds the angiogenic vasculature homing molecule, a structure can be generated using, for example, the program CONCORD (Rusinko et al., *J. Chem. Inf. Comput. Sci.* 29:251 (1989)). Another database, the Available Chemicals Directory (Molecular Design Limited, Informations Systems; San Leandro Calif.), contains about 100,000 compounds that are commercially available and can be screened to identify an angiogenic vasculature homing molecule according to a method of the invention.

Methods for preparing libraries containing diverse populations of various types of molecules such as peptides, peptoids and peptidomimetics are well known in the art and various libraries are commercially available (see, for example, Ecker and Crooke, *Biotechnology* 13:351–360 (1995), and Blondelle et al., *Trends Anal. Chem.* 14:83–92 (1995), and the references cited therein, each of which is incorporated herein by reference; see, also, Goodman and Ro, *Peptidomimetics for Drug Design*, in "Burger's Medicinal Chemistry and Drug Discovery" Vol. 1 (ed. M. E. Wolff; John Wiley & Sons 1995), pages 803–861, and Gordon et al., *J. Med. Chem.* 37:1385–1401 (1994), each of which is incorporated herein by reference). Where a molecule is a peptide, protein or fragment thereof, the molecule can be produced in vitro directly or can be expressed from a nucleic acid, which can be produced in vitro. Methods of synthetic peptide and nucleic acid chemistry are well known in the art.

Particularly useful libraries of molecules to be screened for specific binding to an NG2/HM proteoglycan and, therefore, for activity in homing to angiogenic vasculature, include phage display libraries. Such phage display libraries of molecules include a linear decapeptide library as described in Example I.

In vitro screening of phage libraries previously has been used to identify peptides that bind to antibodies or to cell surface receptors (Smith and Scott (*Meth. Enzymol.* 217:228–257 (1993)). For example, in vitro screening of phage peptide display libraries has been used to identify novel peptides that specifically bound to integrin adhesion receptors (Koivunen et al., *J. Cell Biol.* 124:373–380 (1994a), which is incorporated herein by reference) and to the human urokinase receptor (Goodson et al., *Proc. Natl. Acad. Sci., USA* 91:7129–7133 (1994)).

The use of a phage display library to identify angiogenic vasculature homing molecules that bind to NG2-HM proteoglycan is exemplified herein (Example I). However, phage libraries that display protein receptor molecules, including, for example, an antibody or an antigen binding fragment of an antibody such an Fv, Fd or Fab fragment; a hormone receptor such as a growth factor receptor; or a cell adhesion receptor such as an integrin or a selectin also can be used to practice the invention. Variants of such molecules can be constructed using well known methods such as random, site-directed or codon based mutagenesis (see Huse, U.S. Pat. No. 5,264,563, issued Nov. 23, 1993, which is incorporated herein by reference) and, if desired, peptides can be chemically modified following expression of the phage but prior to administration to the subject. Thus, various types of phage display libraries can be screened.

Phage display technology provides a means for expressing a diverse population of random or selectively randomized peptides. Various methods of phage display and methods for producing diverse populations of peptides are well known in the art. For example, Ladner et al. (U.S. Pat. No. 5,223,409, issued Jun. 29, 1993, which is incorporated herein by reference) describe methods for preparing diverse populations of binding domains on the surface of a phage. In particular, Ladner et al. describe phage vectors useful for producing a phage display library, as well as methods for selecting potential binding domains and producing randomly or selectively mutated binding domains.

Similarly, Smith and Scott (*Meth. Enzymol.* 217:228–257 (1993); see, also, Scott and Smith, *Science* 249: 386–390 (1990), each of which is incorporated herein by reference) describe methods of producing phage peptide display libraries, including vectors and methods of diversifying the population of peptides that are expressed (see, also, Huse, WO 91/07141 and WO 91/07149, each of which is incorporated herein by reference). Phage display technology can be particularly powerful when used, for example, with a codon based mutagenesis method, which can be used to produce random peptides or randomly or desirably biased peptides (Huse, U.S. Pat. No. 5,264,563, supra, 1993). These or other well known methods can be used to produce a phage display library, which can be subjected to the panning methods of the invention in order to identify a peptide that homes to angiogenic vasculature.

In addition to screening a phage display library, panning can be used to screen various other types of libraries, including, for example, an RNA or DNA library or a chemical library. A library of molecules also can be produced, for example, by constructing a cDNA expression library from mRNA collected from a cell, tissue, organ or organism of interest. Methods for producing such libraries are well known in the art (see, for example, Sambrook et al., *Molecular Cloning: A laboratory manual* (Cold Spring Harbor Laboratory Press 1989), which is incorporated herein by reference). Preferably, a peptide encoded by the cDNA is expressed on the surface of a cell or a virus containing the cDNA. For example, cDNA can be cloned into a phage vector wherein, upon expression, the encoded peptide is expressed as a fusion protein on the surface of the phage (see Example I).

In addition, a library of molecules can comprise a library of nucleic acid molecules, which can be DNA or RNA or an analog thereof. Nucleic acid molecules that bind, for example, to a cell surface receptor are well known (see, for example, O'Connell et al., *Proc. Natl. Acad. Sci., USA* 93:5883–5887 (1996); Tuerk and Gold, *Science* 249:505–510 (1990); Gold et al., *Ann. Rev. Biochem.* 64:763–797 (1995), each of which is incorporated herein by reference). Thus, a library of nucleic acid molecules can be contacted with a substantially purified NG2/HM proteoglycan to identify an angiogenic vasculature homing molecule. If desired, the nucleic acid molecules can be nucleic acid analogs that, for example, are less susceptible to attack by nucleases (see, for example, Jelinek et al., *Biochemistry* 34:11363–11372 (1995); Latham et al., *Nucl. Acids Res.* 22:2817–822 (1994); Tam et al., *Nucl. Acids Res.* 22:977–986 (1994); Reed et al., *Cancer Res.* 59:6565–6570 (1990), each of which is incorporated herein by reference).

Monoclonal or polyclonal antibodies exhibiting specific binding to an NG2/HM proteoglycan can be generated by methods well known to those skilled in the art (Harlow and Lane, *Antibodies: A laboratory manual* (Cold Spring Harbor Laboratory Press 1988), which is incorporated herein by reference). Alternatively, libraries of functional antibody fragments such as Fv, single chain Fv or Fab fragments, which can bind to a NG2/HM proteoglycan, can also be screened to identify a homing molecule that binds to a NG2/HM proteoglycan. For example, a combinatorial scFv library generated by immunizing with human tumor xenografts or a substantially purified NG2/HM proteoglycan can be screened for binding to a NG2/HM proteoglycan.

In addition to screening phage and DNA libraries as described above, combinatorial chemistry libraries also can be screened in vitro using a substantially purified NG2/HM proteoglycan according to a method of the invention. Methods for generating combinatorial libraries are well known in the art as described, for example, in Gordon et al., *J. Med.*

Chem. 37:1385–1401 (1994); Gallop et al., *J. Med. Chem.* 37:1203–1251 (1994); and Wilson and Czarnik, eds., *Combinatorial Chemistry* John Wiley & Sons, New York (1997), each of which is incorporated herein by reference.

Angiogenic vasculature homing molecules that are peptidomimetics can be identified by screening a library of peptidomimetics for binding activity to NG2/HM proteoglycan. In addition, a screening assay comprising a competitive binding assay for the NG2/HM proteoglycan and, for example, the natural ligand for the NG2/HM proteoglycan or an angiogenic vasculature homing peptide that specifically binds the NG2/HM proteoglycan also provides a means to identify peptidomimetics that function as angiogenic vasculature homing molecules. As discussed above, such peptidomimetics can provide advantages over angiogenic vasculature homing peptides in that they can be small, relatively stable for storage, conveniently produced in suitable quantities, and capable of being administered orally. A peptidomimetic of an angiogenic vasculature homing peptide can be identified by screening libraries of peptidomimetics in a competitive binding assay as described above.

The presence of a homing molecule that specifically binds a NG2/HM proteoglycan within a library of molecules can be identified using various screening methods well known in the art. Generally, the compounds in a library can be tested individually, for example, using high throughput screening. Methods of in vitro screening are well known in the art. For example, a NG2/HM proteoglycan can be contacted with a library of molecules and screened for binding in vitro. If desired, the NG2/HM proteoglycan can be immobilized, for example, to a solid support such as a bead or plate. A NG2/HM proteoglycan can be directly bound to the support, through covalent or non-covalent interactions, or can be immobilized indirectly through a molecule that binds to the NG2/HM proteoglycan. For example, an antibody that binds to a NG2/HM proteoglycan can be used to immobilize a NG2/HM proteoglycan. The library is contacted with the NG2/HM proteoglycan in vitro and screened for binding activity (see Example I). A library with tagged molecules are particularly useful for identifying molecules-that bind to a NG2/HM proteoglycan.

If desired, the angiogenic vasculature homing molecule can be tagged, which can facilitate recovery or identification of the molecule. Such tagged libraries are useful for in vivo and in vitro screening. As used herein, the term "tag" means a physical, chemical or biological moiety such as a plastic microbead, an oligonucleotide or a bacteriophage, respectively, that is linked to a molecule of the library. Methods for tagging a molecule are well known in the art (Hermanson, *Bioconjugate Techniques* (Academic Press 1996), which is incorporated herein by reference).

A tag, which can be a shared tag or a specific tag, can be useful for identifying the presence or structure of an angiogenic vasculature homing molecule of a library. As used herein, the term "shared tag" means a physical, chemical or biological moiety that is common to each molecule in a library. Biotin, for example, can be a shared tag that is linked to each molecule in a library. A shared tag can be useful to identify the presence of a molecule of the library in a sample and also can be useful to substantially isolate the molecules from a sample. For example, where the shared tag is biotin, the biotin-tagged molecules in a library can be substantially isolated by binding to streptavidin or avidin affinity matrix, or their presence can be identified by binding with a labeled streptavidin. Where a library is a phage display library, the phage that express the peptides are another example of a shared tag, since each peptide of the library is linked to a phage. In addition, a peptide such as the hemaglutinin antigen an be a shared tag that is linked to each molecule in a library, thereby allowing the use of an antibody specific for the hemaglutinin antigen to substantially isolate molecules of the library from a sample of a selected tumor. Furthermore, a molecule or a support containing a molecule can be linked to a hapten such as 4-ethoxy-methylene-2-phenyl-2-oxazoline-5-one (phOx), which can be bound by an anti-phOx antibody linked to a magnetic bead as a means to recover the molecule. Methods for purifying biotin or phOx labeled conjugates are known in the art, and the materials for performing these procedures are commercially available (e.g., Invitrogen, La Jolla Calif., and Promega Corp., Madison Wis.).

A shared tag also can be a nucleic acid sequence that can be useful to identify the presence of molecules of the library in a sample or to substantially isolate molecules of a library from a sample. For example, each of the molecules of a library can be linked to the same selected nucleotide sequence, which constitutes the shared tag. An affinity column containing a nucleotide sequence that is complementary to the shared tag then can be used to hybridize molecules of the library containing the shared tag, thus substantially isolating the molecules from a tumor sample. A nucleotide sequence complementary to a portion of the shared nucleotide sequence tag also can be used as a PCR primer such that the presence of molecules containing the shared tag can be identified in a sample by PCR. Where an angiogenic vasculature homing molecule is a nucleic acid or is tagged with a nucleic acid, an assay such as PCR can be particularly useful for identifying the presence of the molecule because, in principle, PCR can detect the presence of a single nucleic acid molecule (see, for example, Erlich, *PCR Technology: Principles and Applications for DNA Amplification* (Stockton Press 1989); Dieffenbach and Dveksler, *PCR Primer: A Laboratory Manual*, Cold Spring Harbor Press, 1995), each of which is incorporated herein by reference).

A specific tag can be particularly useful in the methods of the invention for identifying an angiogenic vasculature homing molecule that homes to angiogenic vasculature. As used herein, the term "specific tag" means a physical, chemical or biological tag that is linked to a particular molecule in a library and is unique for that particular molecule. A specific tag is particularly useful if it is readily identifiable. A nucleotide sequence that is unique for a particular molecule of a library is an example of a specific tag. For example, the method of synthesizing peptides tagged with a unique nucleotide sequence provides a library of molecules, each containing a specific tag, such that upon determining the nucleotide sequence, the identity of the peptide is known (see Brenner and Lerner, *Proc. Natl. Acad. Sci., USA* 89:5381–5383 (1992), which is incorporated herein by reference). The use of a nucleotide sequence as a specific tag for a peptide or other type of molecule provides a simple means to identify the presence of the molecule in a sample because an extremely sensitive method such as PCR can be used to determine the nucleotide sequence of the specific tag, thereby identifying the sequence of the molecule linked thereto. Similarly, the nucleic acid sequence encoding a peptide expressed on a phage is another example of a specific tag, since sequencing of the specific tag identifies the amino acid sequence of the expressed peptide.

The presence of a shared tag or a specific tag can provide a means to identify or recover an angiogenic vasculature homing molecule of the invention following screening for a molecule that binds, for example, to NG2/HM proteoglycan.

In addition, the combination of a shared tag and specific tag can be particularly useful for identifying an angiogenic vasculature homing molecule.

A tag also can serve as a support. As used herein, the term "support" means a tag having a defined surface to which a molecule can be attached. In general, a tag useful as a support is a shared tag. For example, a support can be a biological tag such as a virus or virus-like particle such as a bacteriophage ("phage"); a bacterium such as E. coil; or a eukaryotic cell such as a yeast, insect or mammalian cell; or can be a physical tag such as a liposome or a microbead, which can be composed of a plastic, agarose, gelatin or other biological or inert material. If desired, a shared tag useful as a support can have linked thereto a specific tag. Thus, the phage display libraries used in the exemplified methods can be considered to consist of the phage, which is a shared tag that also is a support, and the nucleic acid sequence encoding the expressed peptide, the nucleic acid sequence being a specific tag.

In general, a support should have a diameter less than about 10 μm to about 50 μm in its shortest dimension, such that the support can pass relatively unhindered through the capillary beds present in the subject and not occlude circulation. In addition, a support can be nontoxic, so that it does not perturb the normal expression of cell surface molecules or normal physiology of the subject, and biodegradable.

Where a molecule is linked to a support, the molecule is attached to the surface of the support such that the part of the molecule suspected of being able to interact with a target molecule is positioned so as to be able to participate in the interaction. For example, the angiogenic vasculature homing molecule is attached to a support so it can interact with a substantially isolated NG2/HM proteoglycan or with a NG2/HM proteoglycan on a cell in the tumor. If desired, an appropriate spacer molecule can be positioned between the molecule and the support such that the ability of the angiogenic vasculature homing molecule to interact with the target molecule is not hindered. A spacer molecule also can contain a reactive group, which provides a convenient and efficient means of linking a molecule to a support and, if desired, can contain a tag, which can facilitate recovery or identification of the molecule (see Hermanson, supra, 1996).

As exemplified herein, peptides that bind to NG2/HM proteoglycan were identified using phage display of linear decapeptides as peptide fusions. Thus, a molecule having a shared tag was formed by the linking of a peptide to a phage, wherein the phage provided a biological support, the peptide molecule was linked as a fusion protein, the phage-encoded portion of the fusion protein acted as a spacer molecule, and the nucleic acid encoding the peptide provided a specific tag allowing identification of an angiogenic vasculature homing peptide.

If molecules that bind to the target molecule are initially identified by in vitro panning or screening, these newly identified molecules can be tested in vivo to determine if the newly identified molecules can bind to the target molecule and home to angiogenic vasculature in vivo. For example, a newly identified molecule that binds to a NG2/HM proteoglycan can be further characterized by screening the molecule in vivo using the methods described herein and confirming that the newly identified molecule can home to angiogenic vasculature.

Selective homing to a target molecule in vivo can be distinguished from nonspecific binding by detecting differences in the ability of an angiogenic vasculature homing molecule to home to angiogenic vasculature (see Example IV). For example, if the angiogenic vasculature homing molecule is tagged with a phage, selective homing can be identified by combining an angiogenic vasculature homing peptide expressed on a phage with a large excess of non-infective phage or with about a five-fold excess of phage expressing unselected peptides, injecting the mixture into a subject and collecting a sample of the tumor. In the latter case, for example, provided the number of injected phage expressing an angiogenic vasculature homing peptide is sufficiently low so as to be nonsaturating for the target molecule, a determination that greater than about 20% of the phage in the tumor express the angiogenic vasculature homing molecule is demonstrative evidence that the peptide expressed by the phage is a specific angiogenic vasculature homing molecule. In addition, nonspecific localization can be distinguished from selective homing by performing competition experiments using, for example, phage expressing an angiogenic vasculature homing peptide in combination with an excess amount of the "free" peptide.

Selective homing to a target molecule can be demonstrated by showing that molecules that home to NG2/HM proteoglycan, as identified by in vitro panning, are enriched for angiogenic vasculature homing molecules that bind to NG2/HM proteoglycan when administered in vivo. Selective homing to angiogenic vasculature can be further demonstrated by determining the specificity of an angiogenic vasculature homing molecule that binds NG2/HM proteoglycan for angiogenic vasculature as compared to a control organ or tissue.

Molecules that bind to NG2/HM proteoglycan can be confirmed as angiogenic vasculature homing molecules by in vivo targeting using, for example, a mouse containing a transplanted tumor. Such a transplanted tumor can be, for example, a human tumor that is transplanted into immunodeficient mice such as nude mice or a murine tumor that is maintained by passage in tissue culture or in mice. Due to the conserved nature of cellular receptors and of ligands that bind a particular receptor, it is expected that angiogenic vasculature and histologically similar tumor cells in various species can share common cell surface markers useful as target molecules for an angiogenic vasculature homing molecule. Thus, the skilled artisan would recognize that an angiogenic vasculature homing molecule identified in a mouse having a murine tumor of a defined histological type such as a melanoma also would bind to the corresponding target molecule in a tumor in a human or other species. Similarly, tumors growing in experimental animals require associated neovascularization, just as that required for a tumor growing in a human or other species. Thus, an angiogenic vasculature homing molecule that binds a target molecule present in the vasculature in a tumor grown in a mouse likely also can bind to the corresponding target molecule in the vasculature of a tumor in a human or other mammalian subject.

An angiogenic vasculature homing molecule determined in an experimental animal such as a mouse readily can be examined for the ability to bind to a corresponding tumor in a human patient by demonstrating, for example, that the molecule also can bind specifically to a sample of the tumor obtained from the patient. Routine methods can be used to confirm that an angiogenic vasculature homing molecule that homes to angiogenic vasculature in an experimental animal also can bind the target molecule in angiogenic vasculature of a human.

The steps of contacting a target molecule such as a substantially purified NG2/HM proteoglycan with a library and identifying the molecules that bind the target comprise a single round of in vitro panning or screening. Similarly, the steps of administering a library to a subject, collecting a selected tissue containing angiogenic vasculature and identifying the molecules that home to the angiogenic vasculature, comprise a single round of in vivo panning. Although not required, one or more additional rounds of in vitro or in vivo panning generally are performed. Where an additional round of panning is performed, the molecules recovered from the previous round are administered in the second round.

The term "control organ or tissue" is used to mean an organ or tissue other than the tumor for which the identification of an angiogenic vasculature homing molecule is desired. A control organ or tissue is characterized in that an angiogenic vasculature homing molecule does not selectively home to the control organ. A control organ or tissue can be collected, for example, to identify nonspecific binding of the molecule or to determine the selectivity of homing of the molecule. In addition, nonspecific binding can be identified by administering, for example, a control molecule, which is known not to home to angiogenic vasculature but is chemically similar to a potential angiogenic vasculature homing molecule. Alternatively, where the administered molecules are linked to a support, administration of the supports, alone, also can be used to identify nonspecific binding.

As disclosed herein, specific homing of an angiogenic vasculature homing molecule readily can be identified by examining the angiogenic vasculature, for example, in a selected tumor tissue, and comparing to a corresponding nontumor tissue, as well as to control organs or tissues. For example, immunohistological analysis can be performed on a tumor tissue and corresponding nontumor tissue using an antibody specific for a phage used to display angiogenic vasculature homing peptides. Alternatively, an antibody can be used that is specific for a shared tag that is expressed with the peptide, for example, a FLAG epitope or the like, such detection systems being commercially available.

In the examples provided, the animals were sacrificed to collect the selected tumor and control organ or tissue. It should be recognized, however, that only a part of a tumor need be collected to recover a support containing a molecule that homes to that tumor and, similarly, only part of an organ or tissue need be collected as a control. Thus, a part of a tumor, for example, can be collected by biopsy, such that a molecule such as a peptide expressed by a phage can be administered to the same subject a second time or more, as desired. Where the molecule that is to be administered a second time to the same subject is tagged or linked, for example, to a support, the tag or support should be nontoxic and biodegradable, so as not to interfere with subsequent rounds of screening.

The invention additionally provides a method of inhibiting angiogenesis in a tumor of a subject by administering to the subject a conjugate comprising a moiety linked to an angiogenic vasculature homing molecule that selectively binds a NG2/HM proteoglycan, wherein the angiogenic vasculature homing molecule is not an antibody.

As used herein, the term "tumor" means a mass of cells that are characterized, at least in part, by containing angiogenic vasculature. The term "tumor" is used broadly to include the tumor parenchymal cells as well as the supporting stroma, including the angiogenic blood vessels that infiltrate the tumor parenchymal cell mass. Although a tumor generally is a malignant tumor, i.e., a "cancer," a tumor also can be nonmalignant, provided that neovascularization is associated with the tumor. The term "normal" or "nontumor" tissue is used to refer to tissue that is not a "tumor." As disclosed herein, an angiogenic vasculature homing molecule that homes to a tumor can be identified based on its ability to home to angiogenic vasculature in a tumor, but not to a corresponding nontumor tissue.

As used herein, the term "corresponding," when used in reference to tumors or tissues or both, means that two or more tumors, or two or more tissues, or a tumor and a tissue are of the same histologic type. The skilled artisan will recognize that the histologic type of a tissue is a function of the cells comprising the tissue. Thus, the artisan will recognize, for example, that a nontumor tissue corresponding to a breast tumor is normal breast tissue, whereas a nontumor tissue corresponding to a melanoma is skin, which contains melanocytes. Furthermore, for purposes of the invention, it is recognized that an angiogenic vasculature homing molecule can bind specifically to a target molecule expressed by the vasculature in a tumor, which generally contains blood vessels undergoing neovascularization, in which case a tissue corresponding to the tumor would comprise nontumor tissue containing blood vessels that are not undergoing active angiogenesis.

The term "corresponding" also is used herein in reference to the evolutionarily conserved nature of target molecules, which are expressed in a tumor, for example, in a mouse as compared to a human. Thus, reference to the corresponding target molecules in mouse tumor vasculature as compared, for example, to human vasculature, means target molecules having a similar function, particularly the ability to specifically bind an angiogenic vasculature homing molecule.

Identified angiogenic vasculature homing molecules are useful, for example, for targeting a desired moiety such as a drug, a toxin or a detectable label, which can be linked to the molecule, to a tumor. Thus, the invention provides angiogenic vasculature homing molecule/moiety conjugates, which are useful for targeting the moiety to a tumor. Conjugates of the invention include, for example, the angiogenic vasculature homing molecule TAASGVRSMH (SEQ ID NO:1) and LTLRWVGLMS (SEQ ID NO:2) linked to moieties as described below. Accordingly, the invention also provides methods of targeting a moiety to a tumor and, therefore, methods of reducing the severity of a tumor and of treating a subject having a cancer.

The invention additionally provides a method of targeting a tumor in vivo. The method includes the steps of contacting the tumor with a homing molecule that selectively homes to a NG2/HM proteoglycan, wherein the homing molecule is not an antibody. NG2/HM proteoglycan is also expressed by tumor cells in many types of tumors (Behm et al., supra, 1996; Real et al., supra, 1985; Schrappe et al., supra, 1991; Leger et al., supra, 1994). Therefore, in addition to homing to angiogenic vasculature, a homing molecule that binds NG2/HM proteoglycan is useful for directly targeting a tumor that expresses NG2/HM proteoglycan.

The invention also provides a method of directing an angiogenic vasculature homing molecule to angiogenic vasculature in a non-tumor tissue. The method includes administering a conjugate including a moiety linked to a homing molecule that exhibits specific binding to a NG2/HM proteoglycan, whereby the conjugate is directed to angiogenic vasculature of a non-tumor tissue. Directing an angiogenic vasculature homing molecule to angiogenic vasculature in a non-tumor tissue is useful, for example, for treating diseases involving neovascularized tissue such as retinal neovascularization in macular degeneration and diabetes and neovascularization in rheumatoid arthritis synovium, where inhibition of neovascularization is desirable. Directing an angiogenic vasculature homing molecule to angiogenic vasculature in a non-tumor tissue can also be useful, for example, in wound healing, where it can be advantageous to regulate the activity of a NG2/HM proteoglycan in granulation tissue of healing wounds. One skilled in the art can readily identify a NG2/HM proteoglycan binding molecule that binds to angiogenic vasculature in non-tumor tissue by screening a NG2/HM proteoglycan binding molecule for in vivo binding to angiogenic vasculature in a non-tumor tissue using the in vivo homing methods disclosed herein.

One skilled in the art understands that a molecule that specifically binds a substantially purified NG2/HM proteoglycan can bind and modulate the biological activity of the NG2/HM proteoglycan, or can be inert with respect to its ability to affect the activity of an NG2/HM proteoglycan. A molecule that specifically binds a substantially purified NG2/HM proteoglycan can be an agonist or an inhibitor of the proteoglycan biological activity and, thus, can enhance or inhibit angiogenesis, or the molecule can be linked to a moiety that provides stimulatory or inhibitory activity of angiogenesis.

Once identified, angiogenic vasculature homing molecules can be synthesized in required quantities using routine methods. For example, angiogenic vasculature homing molecules that are peptides can be synthesized using routine methods of solid state peptide synthesis (see, for example, Merrifield (*J. Am. Chem. Soc.* 85:2149 (1964)). Alternatively, angiogenic vasculature homing peptides can be purchased from commercial sources (for example, Anaspec; San Jose Calif.) and a desired moiety can be linked to the molecule. Several methods useful for linking a moiety to a molecule are known in the art, depending on the particular chemical characteristics of the molecule, as described below.

As disclosed herein, angiogenic vasculature homing molecules can be conjugated to moieties such as a drug or toxin in order to target the drug or toxin to angiogenic vasculature. An angiogenic vasculature homing molecule of the invention, for example, TAASGVRSMH (SEQ ID NO:1) or LTLRWVGLMS (SEQ ID NO:2), which bind to a NG2/HM proteoglycan, can be used to direct a moiety to angiogenic vasculature. Additional angiogenic vasculature homing molecules that bind to the NG2/HM proteoglycan identified in vivo or in vitro as described above also can be used to direct a moiety to angiogenic vasculature, for example, in a tumor.

A variety of moieties can be directed to angiogenic vasculature in a method of the invention. As used herein, the term "moiety" is used broadly to mean a physical, chemical, or biological material that is linked to an angiogenic vasculature homing molecule for the purpose of being targeted in vivo to angiogenic vasculature. In particular, a moiety is a biologically useful moiety such as a therapeutic moiety, a diagnostic moiety or a drug delivery vehicle. Thus, a moiety can be a therapeutic agent, for example, a cancer chemotherapeutic agent such as doxorubicin, which, when linked to an angiogenic vasculature homing molecule, provides a conjugate useful for treating a cancer in a subject by targeting the cancer chemotherapeutic agent to angiogenic vasculature in a tumor. In addition, a moiety can be a drug delivery vehicle such as a chambered microdevice, a cell, a liposome or a virus, which can contain an agent such as a drug or a nucleic acid.

A moiety also can be a molecule such as a polypeptide or nucleic acid, to which an angiogenic vasculature homing molecule is grafted for the purpose of directing the polypeptide or nucleic acid to a selected tumor (Smith et al., *J. Biol. Chem.* 269:32788–32795 (1994); Goldman et al., *Cancer Res.* 15:1447–1451 (1997), each of which is incorporated herein by reference). For example, a peptide angiogenic vasculature homing molecule can be expressed as a fusion protein with a desired polypeptide such that the peptide targets the grafted polypeptide to angiogenic vasculature. As used herein, the term "grafted polypeptide" is intended to refer to a fusion of a peptide angiogenic vasculature homing molecule to another peptide. The grafted polypeptide can be a fusion peptide, where the two grafted peptides are linked by a peptide bond. Alternatively, the peptides can be conjugated by covalent crosslinking using methods well known in the art, for example, as described herein. A grafted polypeptide linked by a peptide bond can be expressed from a gene encoding a fusion polypeptide or the grafted polypeptide can be synthesized by peptide synthesis methods well known in the art, as described above.

A desired polypeptide, which is grafted to the angiogenic vasculature homing peptide, can be a polypeptide involved in initiating a cell death pathway, for example, caspase 8, thus providing a means to direct caspase 8 to angiogenic vasculature associated with a tumor, where it can induce apoptosis of the tumor cells or of the vasculature supplying the tumor. An angiogenic vasculature homing peptide also can be grafted to a polypeptide expressed by a virus, for example, the adenovirus penton base coat protein, thus providing a means to target a virus to angiogenic vasculature (Wickham et al., *Gene Ther.* 2:750–756 (1995); Weitzman et al., In: "Gene Therapy and Vector Systems" 2:17–25 (1997), each of which is incorporated herein by reference). Such a grafted virus can contain an exogenous gene useful in a method of gene therapy. Accordingly, the invention provides compositions of matter comprising an angiogenic vasculature homing molecule/moiety conjugate.

A moiety can be a detectable label such as a radiolabel or can be a cytotoxic agent, including a toxin such as ricin or a drug such as a chemotherapeutic agent or can be a physical, chemical or biological material such as a liposome, microcapsule, micropump or other chambered microdevice, which can be used, for example, as a drug delivery system. Generally, such microdevices, should be nontoxic and, if desired, biodegradable. Various moieties, including microcapsules, which can contain an agent, and methods for linking a moiety, including a chambered microdevice, to a molecule of the invention are well known in the art and commercially available (see, for example, "Remington's Pharmaceutical Sciences" 18th ed. (Mack Publishing Co. 1990), chapters 89–91; Harlow and Lane, *Antibodies: A laboratory manual* (Cold Spring Harbor Laboratory Press 1988), each of which is incorporated herein by reference; see, also, Hermanson, supra, 1996).

As disclosed herein, a moiety can be, for example, a cancer chemotherapeutic agent linked to an angiogenic vasculature homing molecule to produce an angiogenic vasculature homing molecule/moiety conjugate. Cytotoxic chemotherapy is the basis of the systemic treatment of disseminated malignant tumors. However, a major limitation of the currently used chemotherapeutic agents is that these drugs have the narrowest therapeutic index in all of medicine. As such, the dose of cancer chemotherapeutic agents generally is limited by undesirable toxicity to the patient being treated.

The skilled artisan will recognize that various chemotherapeutic agents such as doxorubicin can be linked to an angiogenic vasculature homing molecule to make a conjugate of the invention. Cancer chemotherapeutic agents have been linked to antibodies, for example, for the purpose of targeting the agents to cells such as tumor cells that express the antigen recognized by the antibodies. In addition, in such antibody/drug conjugates, the agent can maintain its therapeutic function and the antibody can maintain its antigen binding specificity. For example, the anthracyclin, doxorubicin, has been linked to antibodies and the antibody/doxorubicin conjugates have been therapeutically effective in treating tumors (Sivam et al., *Cancer Res.* 55:2352–2356 (1995); Lau et al., *Bioorg. Med. Chem.* 3:1299–1304 (1995); Shih et al., *Cancer Immunol. Immunother.* 38:92–98 (1994)). Similarly, other anthracyclins, including idarubicin and daunorubicin, have been chemically conjugated to antibodies, which have delivered effective doses of the agents to tumors (Rowland et al., *Cancer Immunol. Immunother.* 37:195–202 (1993); Aboud-Pirak et al., *Biochem. Pharmacol.* 38:641–648 (1989)).

In addition to the anthracyclins, alkylating agents such as melphalan and chlorambucil have been linked to antibodies to produce therapeutically effective conjugates (Rowland et al., *Cancer Immunol. Immunother.* 37:195–202 (1993); Smyth et al., *Immunol. Cell Biol.* 65:315–321 (1987)), as have vinca alkaloids such as vindesine and vinblastine (Aboud-Pirak et al., supra, 1989; Starling et al., *Bioconj. Chem.* 3:315–322 (1992)). Similarly, conjugates of antibodies and antimetabolites such as 5-fluorouracil, 5-fluorouridine and derivatives thereof have been effective in treating tumors (Krauer et al., *Cancer Res.* 52:132–137 (1992); Henn et al., *J. Med. Chem.* 36:1570–1579 (1993)). Other chemotherapeutic agents, including cis-platinum (Schechter et al., *Int. J. Cancer* 48:167–172 (1991)), methotrexate (Shawler et al., *J. Biol. Resp. Mod.* 7:608–618 (1988); Fitzpatrick and Garnett, *Anticancer Drug Des.* 10:11–24 (1995)) and mitomycin-C (Dillman et al., *Mol. Biother.* 1:250–255 (1989)) also are therapeutically effective when administered as conjugates with various different antibodies.

The results obtained using antibody/drug conjugates demonstrate that a chemotherapeutic agent can be linked to an antibody to produce a conjugate that maintains the antigen binding specificity of the antibody and the therapeutic function of the agent. Similarly, a conjugate comprising an angiogenic vasculature homing molecule linked to a therapeutic agent can maintain the homing specificity of the angiogenic vasculature homing molecule as well as the therapeutic efficacy of the therapeutic agent.

Since the moiety component of an angiogenic vasculature homing molecule/moiety conjugate can comprise a substantial portion of the conjugate without adversely affecting the ability of the angiogenic vasculature homing molecule to home to angiogenic vasculature, additional components can be included as part of the conjugate, if desired. For example, in some cases, it can be desirable to utilize an oligopeptide spacer between an angiogenic vasculature homing peptide and the moiety (Fitzpatrick and Garnett, *Anticancer Drug Des.* 10:1–9 (1995)). In this way, panels of moiety/spacer complexes can be constructed, in which a common spacer is linked to various different moieties. Such panels of moiety/spacer conjugates can facilitate linkage of the moiety to an angiogenic vasculature homing molecule.

Doxorubicin is one of the most commonly used cancer chemotherapeutic agents and, particularly, is used for treating breast cancer (Stewart and Ratain, In: "Cancer: Principles and practice of oncology" 5th ed., chap. 19 (eds. DeVita, Jr., et al.; *J. P. Lippincott* 1997); Harris et al., In "Cancer: Principles and practice of oncology," supra, 1997).

In addition, doxorubicin has anti-angiogenic activity (Steiner, In "Angiogenesis: Key principles-Science, technology and medicine," pp. 449–454 (eds. Steiner et al.; Birkhauser Verlag, 1992)), which can contribute to its effectiveness in treating cancer.

The linking of a moiety to an angiogenic vasculature homing molecule can result in the molecule directing homing of the linked moiety to the angiogenic vasculature of a tumor. For example, the linking of a brain homing peptide to a RBC directed homing of the RBC to brain (see U.S. Pat. No. 5,622,699; Pasqualini and Ruoslahti, *Nature* 380:364–366 (1996)). This result indicates that an angiogenic vasculature homing molecule of the invention also can be linked to cell type or to a physical, chemical or biological delivery system such as a liposome or other encapsulating device, which can contain an agent such as drug, in order to direct the cell type or the delivery system to a selected tumor. For example, an angiogenic vasculature homing molecule can be linked to a white blood cell (WBC) such as a cytotoxic T cell or a killer cell, wherein upon administration of the angiogenic vasculature homing molecule/WBC conjugate, the molecule directs homing of the WBC to the tumor, where the WBC can exert its effector function. Similarly, an angiogenic vasculature homing molecule can be linked to a liposome or to a chambered microdevice comprising, for example, a permeable or semipermeable membrane, wherein an agent such as a drug to be delivered to a selected tumor is contained within the liposome or microdevice. Such compositions also can be useful, for example, for delivering a nucleic acid molecule to tumor cells, thereby providing a means for performing in vivo targeted gene therapy.

It is recognized that, in some cases, a drug can lose cytotoxic efficacy upon conjugation or derivatization depending, for example, on the conjugation procedure or the chemical group utilized (Hurwitz et al., *Cancer Res.* 35:1175–1181 (1975); Trail et al., *Science* 261;212–215 (1993); Nagy et al., *Proc. Natl. Acad. Sci., USA* 93:7269–7273 (1996)). Moreover, it is recognized that a phage that yields an angiogenic vasculature homing peptide of the invention displays as many as five of the peptides. Thus, there is a possibility that the affinity of an individual angiogenic vasculature homing molecule is too low for effective angiogenic vasculature or tumor homing and that multivalent, rather than univalent, conjugates of the angiogenic vasculature homing molecule must be used.

A moiety such as a therapeutic or diagnostic agent can be conjugated to an angiogenic vasculature homing peptide using, for example, carbodiimide conjugation (Bauminger and Wilchek, *Meth. Enzymol.* 70:151–159 (1980), which is incorporated herein by reference). Alternatively, a moiety can be coupled to a homing molecule as described by Nagy et al., supra, 1996; and Nagy et al., *Proc. Natl. Acad. Sci. USA* 95:1794–1799 (1998), each of which is incorporated herein by reference. In addition, methods of linking haptens to carrier proteins are used routinely in the field of applied immunology (see, for example, Harlow and Lane, supra, 1988; Hermanson, supra, 1996).

Carbodiimides comprise a group of compounds that have the general formula R—N=C=N—R', where R and R' can be aliphatic or aromatic, and are used for synthesis of peptide bonds. The preparative procedure is simple, relatively fast, and is carried out under mild conditions. Carbodiimide compounds attack carboxylic groups to change them into reactive sites for free amino groups. Carbodiimide conjugation has been used to conjugate a variety of compounds to carriers for the production of antibodies.

The water soluble carbodiimide, 1-ethyl-3-(3-dimethylaminopropyl)carbodiimide (EDC) is particularly useful for conjugating a moiety to an angiogenic vasculature homing peptide. The conjugation of doxorubicin and an angiogenic vasculature homing peptide requires the presence of an amino group, which is provided by doxorubicin, and a carboxyl group, which is provided by the peptide.

In addition to using carbodiimides for the direct formation of peptide bonds, EDC also can be used to prepare active esters such as N-hydroxysuccinimide (NHS) ester. The NHS ester, which binds only to amino groups, then can be used to induce the formation of an amide bond with the single amino group of the doxorubicin. The use of EDC and NHS in combination is commonly used for conjugation in order to increase yield of conjugate formation (Bauminger and Wilchek, supra, 1980).

Other methods for conjugating a moiety to an angiogenic vasculature homing molecule also can be used. For example, sodium periodate oxidation followed by reductive alkylation of appropriate reactants can be used, as can glutaraldehyde crosslinking. However, it is recognized that, regardless of which method of producing a conjugate of the invention is selected, a determination must be made that the angiogenic vasculature homing molecule maintains its targeting ability and that the moiety maintains its relevant function. Methods known in the art can confirm the activity of the moiety/angiogenic vasculature homing molecule conjugate.

The yield of moiety/angiogenic vasculature homing molecule conjugate formed is determined using routine methods. For example, HPLC or capillary electrophoresis or other qualitative or quantitative method can be used (see, for example, Liu et al., *J. Chromatoar.* 735:357–366 (1996); Rose et al., *J. Chromatoar.* 425:419–412 (1988), each of which is incorporated herein by reference). In particular, the skilled artisan will recognize that the choice of a method for determining yield of a conjugation reaction depends, in part, on the physical and chemical characteristics of the specific moiety and angiogenic vasculature homing molecule. Following conjugation, the reaction products are desalted to remove any free peptide and free drug.

Identified angiogenic vasculature homing molecules are useful, for example, for targeting a desired moiety such as a drug, a toxin or a detectable label, which can be linked to the molecule, to angiogenic vasculature such as angiogenic vasculature associated with a tumor. The angiogenic vasculature homing molecule can be administered to a subject to effect treatment of a patient, for example, to treat a tumor in a patient.

The term "administering to a subject", when used in referring to an angiogenic vasculature homing molecule, is used in its broadest sense to mean that the angiogenic vasculature homing molecule is delivered to angiogenic vasculature in the subject, which, generally, is a vertebrate, particularly a mammal such as a human. An angiogenic vasculature homing molecule can be administered to a tumor containing angiogenic vasculature, for example, to target a drug, toxin or detectable label.

An angiogenic vasculature homing molecule can be administered to a subject, for example, by injecting the angiogenic vasculature homing molecule into the circulation of the subject such that the molecules pass through the angiogenic vasculature such as the angiogenic vasculature in a tumor. Alternatively, a cannula can be inserted into a blood vessel in the subject, such that the angiogenic vasculature homing molecule is administered by perfusion for an appropriate period of time. Similarly, an angiogenic vasculature homing molecule can be shunted through one or a few organs, including the tumor, by cannulation of the appropriate blood vessels in the subject.

In some cases, a molecule can localize nonspecifically to an organ or tissue containing a tumor. For example, high background binding can occur in organs such as liver and spleen, which contain a marked component of the reticuloendothelial system (RES). Various methods can be used to prevent nonspecific binding of a molecule to an organ containing a component of the RES. For example, a molecule that homes selectively to a tumor present in an organ containing a component of the RES can be obtained by first blocking the RES using, for example, polystyrene latex particles or dextran sulfate (see Kalin et al., *Nucl. Med. Biol.* 20:171–174 (1993); Illum et al., *J. Pharm. Sci.* 75:16–22 (1986); Takeya et al., *J. Gen. Microbiol.* 100:373–379 (1977), each of which is incorporated herein by reference), then administering the library to the subject. For example, pre-administration of dextran sulfate 500 or polystyrene microspheres prior to administration of a test substance has been used to block nonspecific uptake of the test substance by Kupffer cells, which are the RES component of the liver (Illum et al., supra, 1986). Similarly, nonspecific uptake of agents by the RES has been blocked using carbon particles or silica (Takeya et al., supra, 1977) or a gelatine colloid (Kalin et al., supra, 1993). Thus, various agents useful for blocking nonspecific uptake by the RES are known and routinely used.

Nonspecific binding of a virus moiety linked to an angiogenic vasculature homing molecule to RES or to other sites also can be prevented by coinjecting, for example, with the same virus made noninfective. In addition, a virus moiety selected for linking to an angiogenic vasculature homing molecule can be selected to exhibit low background binding to the particular organ. For example, Merrill et al. (*Proc. Natl. Acad. Sci., USA* 93:3188–3192 (1996), which is incorporated herein by reference) selected lambda-type phage that are not taken up by the RES and, as a result, remain in the circulation for a prolonged period of time.

In some cases, the metastasis of cancer cells to specific organs can be due to recognition by the tumor cell of an organ specific marker, including organ specific endothelial cell markers (Fidler and Hart, *Science* 217:998–1003 (1982)). The pattern of metastasis of many cancers can be explained by assuming that circulating tumor cells are preferentially trapped in the first vascular bed encountered. Thus, the lungs and the liver are the most frequent sites of cancer metastasis. However, some cancers show patterns of metastasis that are not explained by circulatory routing. Metastasis of such cancers may be due to the presence of selectively expressed address molecules such as endothelial cell surface molecules expressed in the organ to which the cancer metastasizes (see Goetz et al., *Int. J. Cancer* 65:192–199 (1996); Zhu et al., *Proc. Natl. Acad. Sci., USA* 88:9568–9572 (1991); Pauli et al., *Cancer Metast. Rev.* 9:175–189 (1990); Nicolson, *Biochim. Biophys. Acta* 948:175–224 (1988)). The identification of molecules that bind to such organ-specific endothelial cell markers can provide a means to prevent tumor cell metastasis to the particular organ.

Angiogenic vasculature homing molecules of the invention, which bind to NG2/HM proteoglycan, can bind to pericytes in angiogenic vasculature, including tumors. The vasculature within tumors is distinct, presumably due to the continual neovascularization, resulting in the formation of new blood vessels required for tumor growth. The distinct properties of the angiogenic neovasculature within tumors are reflected in the presence of specific markers in endothelial cells and pericytes (Folkman, *Nature Biotechnol.* 15:510 (1997b); Risau, *FASEB J.* 9:926–933 (1995); Brooks et al., supra, 1994).

The ability of an angiogenic vasculature homing molecule to target the blood vessels in a tumor provides substantial advantages over methods of systemic treatment or methods that directly target the tumor cells. For example, tumor cells depend on a vascular supply for survival and the endothelial lining of blood vessels is readily accessible to a circulating probe. Conversely, in order to reach solid tumor cells, a chemotherapeutic agent must overcome potentially long diffusion distances, closely packed tumor cells, and a dense fibrous stroma with a high interstitial pressure that impedes extravasation (Burrows and Thorpe, *Pharmacol. Ther.* 64:155–174 (1994)).

In addition, where the tumor vasculature is targeted, the killing of all target cells may not be required, since partial denudation of the endothelium can lead to the formation of an occlusive thrombus halting the blood flow through the entirety of the affected tumor vessel (Burrows and Thorpe, supra, 1994). Furthermore, unlike direct tumor targeting, there is an intrinsic amplification mechanism in tumor vasculature targeting. A single capillary loop can supply nutrients to up to 100 tumor cells, each of which is critically dependent on the blood supply (Denekamp, *Cancer Metast. Rev.* 9:267–282 (1990); Folkman, supra, 1997a).

Furthermore, cells in the angiogenic vasculature of a tumor also are unlikely to lose a cell surface target receptor or develop a drug resistance phenotype, as can develop through mutation and clonal evolution of tumor cells. Endothelial cells are genetically stable despite their high proliferation rates (Burrows and Thorpe, supra, 1994; Folkman, supra, 1995; Folkman, supra, 1997b). In this regard, it has been long recognized by medical oncologists that, while tumors treated with chemotherapeutic agents commonly develop drug resistance, normal tissues such as bone marrow do not develop such resistance. Thus, toxicity to normal tissues such as chemotherapy induced myelosuppression continues to occur during a treatment, even after tumor cells have become drug resistant. Since cells of the angiogenic vasculature supplying a tumor are nontumor cells, it is expected that they will not develop resistance to chemotherapeutic agents, in a manner analogous to bone marrow cells. In fact, drug resistance has not been observed during long term anti-angiogenic therapy in either experimental animals or in clinical trials (Folkman, supra, 1997b; Kerbel, *BioEssays*, 13:31–36 (1991); Kerbel, *Nature* 390:335–336 (1997); Boehm et al., *Nature* 390:404–407 (1997)).

As disclosed herein, NG2/HM proteoglycan is expressed in pericytes located in angiogenic vasculature. Moreover, the pericytes expressing NG2/HM proteoglycan are accessible to angiogenic vasculature homing molecules that bind to NG2/HM proteoglycan, even when the angiogenic vasculature homing molecule is attached to relatively bulky tags such as phage (Example IV). Because phage are relatively large particles and are not likely to be able to penetrate an intact endothelial layer in the short time used for the homing experiment described herein, the results demonstrate that pericytes in angiogenic vasculature of tumor vessels are accessible to circulating probes, possibly due to "leaky" tumor essels (Blood and Zetter, *Biochem. Biophys. Acta,* 032:89–118 (1990); Nagy et al., *Biochem. Biophys. Acta* 948:305–326 (1989); Dvorak et al., *Am. J. Pathol.* 133:95–109 (1989)). Thus, the localization and accessibility of NG2/HM proteoglycan on pericytes supports the use of angiogenic vasculature homing molecules that bind to NG2/HM proteoglycan for targeting angiogenic vasculature in a tumor.

Furthermore, administration of an angiogenic vasculature homing molecule that binds to NG2/HM proteoglycan can be effective at targeting a drug or toxin to angiogenic vasculature alone, or can be combined with other therapeutic compounds to treat a patient with a tumor. For example, the angiogenic vasculature homing molecules of the present invention, which bind to NG2/HM proteoglycan, can be advantageously combined with therapies directed to endothelial cells of angiogenic vasculature. Furthermore, since NG2/HM proteoglycan is expressed in certain types of tumors, the angiogenic vasculature homing molecules of the invention that bind to NG2/HM proteoglycan can target tumors directly as well as angiogenic vasculature associated with tumors (Behm et al., supra, 1996; Real et al., supra, 1985; Schrappe et al., supra, 1991; Leger et al., supra, 1994).

When administered to a subject, the angiogenic vasculature homing molecule/moiety conjugate is administered as a pharmaceutical composition containing, for example, the conjugate and a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive oil or injectable organic esters.

A pharmaceutically acceptable carrier can contain physiologically acceptable compounds that act, for example, to stabilize or to increase the absorption of the conjugate. Such physiologically acceptable compounds include, for example, carbohydrates, such as glucose, sucrose or dextrans, antioxidants, such as ascorbic acid or glutathione, chelating agents, low molecular weight proteins or other stabilizers or excipients. One skilled in the art would know that the choice of a pharmaceutically acceptable carrier, including a physiologically acceptable compound, depends, for example, on the route of administration of the composition. The pharmaceutical composition also can contain an agent such as a cancer therapeutic agent.

One skilled in the art would know that a pharmaceutical composition containing an angiogenic vasculature homing molecule can be administered to a subject by various routes including, for example, orally or parenterally, such as intravenously. The composition can be administered by injection or by intubation. The pharmaceutical composition also can be an angiogenic vasculature homing molecule linked to liposomes or other polymer matrices, which can have incorporated therein, for example, a drug such as a chemotherapeutic agent (Gregoriadis, *Liposome Technology*, Vols. I to III, 2nd ed. (CRC Press, Boca Raton Fla. (1993), which is incorporated herein by reference). Liposomes, for example, which consist of phospholipids or other lipids, are nontoxic, physiologically acceptable and metabolizable carriers that are relatively simple to make and administer.

For the diagnostic or therapeutic methods disclosed herein, an effective amount of the angiogenic vasculature homing molecule/moiety conjugate must be administered to the subject. As used herein, the term "effective amount" means the amount of the conjugate that produces the desired effect. An effective amount often will depend on the moiety linked to the angiogenic vasculature homing molecule. Thus, a lesser amount of a radiolabeled molecule can be required for imaging as compared to the amount of a drug/molecule conjugate administered for therapeutic purposes. An effective amount of a particular molecule/moiety for a specific purpose can be determined using methods well known to those in the art.

The route of administration of an angiogenic vasculature homing molecule will depend, in part, on the chemical structure of the molecule. Peptides, for example, are not particularly useful when administered orally because they can be degraded in the digestive tract. However, methods for chemically modifying peptides to render them less susceptible to degradation by endogenous proteases or more absorbable through the alimentary tract are well known (see, for example, Blondelle et al., supra, 1995; Ecker and Crooke, supra, 1995; Goodman and Ro, supra, 1995). In addition, methods for preparing libraries of peptidomimetics, which can contain D-amino acids, other non-naturally occurring amino acids, or chemically modified amino acids; or can be organic molecules that mimic the structure of peptide; or can be peptoids such as vinylogous peptoids, are known in the art and can be used to identify molecules that home to a NG2/HM proteoglycan and are stable for oral administration.

The invention also provides a method of identifying the presence of a NG2/HM proteoglycan. The method includes the steps of contacting a sample with an angiogenic vasculature homing molecule, wherein the angiogenic vasculature homing molecule binds to a NG2/HM proteoglycan and wherein the angiogenic vasculature homing molecule is not an antibody, and detecting specific binding of the angiogenic vasculature homing molecule to the sample, where the binding identifies the presence of the NG2/HM proteoglycan.

An angiogenic vasculature homing molecule is useful, for example, for targeting a desired moiety to the angiogenic vasculature in a tumor as discussed above. In addition, an angiogenic vasculature homing molecule can be used to identify the presence of a target molecule in a sample. As used herein, the term "sample" is used in its broadest sense to mean a cell, tissue, organ or portion thereof, including a tumor, that is isolated from the body. A sample can be, for example, a histologic section or a specimen obtained by biopsy or cells that are placed in or adapted to tissue culture. If desired, a sample can be processed, for example, by homogenization, which can be an initial step for isolating the target molecule to which a homing molecule binds.

The invention additionally provides a method of imaging the angiogenic vasculature in a subject. The method includes the steps of administering to the subject a conjugate comprising a detectable moiety linked to an angiogenic vasculature homing molecule that exhibits binding to a NG2/HM proteoglycan, wherein the angiogenic vasculature homing molecule is not an antibody, and detecting the conjugate.

In one embodiment, an angiogenic vasculature homing molecule is linked to a moiety that is detectable external to the subject, thereby providing a composition useful to perform an in vivo diagnostic imaging study. For example, in vivo imaging using a detectably labeled angiogenic vasculature homing peptide can be used to identify the presence of angiogenic vasculature associated with a tumor in a subject. For such studies, a moiety such as a gamma ray emitting radionuclide, for example, indium-111 or technitium-99, can be linked to the angiogenic vasculature homing molecule and, following administration to a subject, can be detected using a solid scintillation detector. Similarly, a positron emitting radionuclide such as carbon-11 or a paramagnetic spin label such as carbon-13 can be linked to the molecule and, following administration to a subject, the localization of the moiety/molecule can be detected using positron emission transaxial tomography or magnetic resonance imaging, respectively. Such methods can identify a primary tumor as well as a metastatic lesion, which may not be detectable using other methods. Having identified the presence of a cancer in a subject, in another embodiment of the invention, the angiogenic vasculature homing molecule is linked to a cytotoxic agent such as ricin or a cancer chemotherapeutic agent such as doxorubicin in order to direct the moiety to the tumor or can be linked to a chambered microdevice, which can contain a chemotherapeutic drug or other cytotoxic agent. Use of such a composition provides a means to selectively kill the tumor, while substantially sparing normal tissues in a cancer patient and, therefore, the conjugates of the invention provide useful medicaments for diagnosing or treating a cancer patient.

The skilled artisan would recognize that various angiogenic vasculature homing molecules can selectively home only to a tumor or can selectively home to a tumor and to a family of selected organs, including, in some cases, the normal tissue counterpart to the tumor. Thus, the artisan would select an angiogenic vasculature homing peptide for administration to a subject based on the procedure being performed. For example, an angiogenic vasculature homing molecule that homes only to a tumor can be useful for directing a therapy to the tumor. In comparison, an angiogenic sovasculature homing molecule that selectively homes not only to the tumor, but also to one or more normal organs or tissues, can be used in an imaging method, whereby homing to an organ or tissue other than the tumor provides an internal imaging control. Such an internal control can be useful, for example, for detecting a change in the size of a tumor in response to a treatment, since the normal organ is not expected to change in size and, therefore, can be compared with the tumor size.

The following examples are intended to illustrate but not limit the present invention.

EXAMPLE I

Isolation of NG2 Binding Phage

This example describes the isolation of phage displaying peptides that bind to NG2.

To identify peptide motifs capable of interacting with NG2, recombinant NG2 fragments consisting of the N-terminal two-thirds of the extracellular domain of NG2 proteoglycan were generated. Briefly, a recombinant fragment of rat NG2 consisting of the N-terminal two-thirds of the extracellular domain (NG2ECΔ3) was purified from transfected human embryonic kidney 293 cells as described (Tillet et al., *J. Biol. Chem.* 272:10769–10776 (1997)). Recombinant NG2 diluted in phosphate buffered saline (PBS) (2 $\mu$g NG2/well) was coated onto microtiter wells overnight at 4° C. Wells were blocked with 2% bovine serum albumin (BSA) in PBS for 1 hr at room temperature. For biopanning, phage ($1\times10^{11}$ TU) from a linear decapeptide phage library diluted in 2% BSA were added to NG2-coated wells and incubated for 2 hr at room temperature. Wells were washed with PBS containing 0.1% TWEEN-20 to remove unbound phage. Bound phage were recovered by direct infection of wells with exponentially growing K91kan bacteria, followed by phage amplification overnight at 37° C. Amplified phage were then subjected to four subsequent rounds of selection on NG2-coated wells. Phage binding was quantified by counting colonies from aliquots of phage-infected bacteria removed from NG2-coated wells. Phage were sequenced from randomly selected clones as described previously (Rajotte et al., *J. Clin. Invest.* 15:430–437 (1998)).

Binding of individual phage clones or an aliquot of unselected phage library control to NG2 or BSA-coated control wells was performed as described above using $1\times10^9$ input phage/well. For competition studies, phage incubations were performed in the presence of increasing concentrations of soluble NG2 or GST-fusion proteins.

To identify peptide motifs capable of interacting with NG2, the recombinant NG2 fragments were used to select phage clones from a random decapeptide phage display library. Bound phage were isolated and used for successive rounds of panning on the NG2 proteoglycan. Five successive rounds of biopanning were performed. Random clones were sequenced from rounds II to V. Sequence analysis from the final three rounds of panning are shown in Table 1. In parentheses is the number of clones displaying the same sequence. The sequences shown in column III of Table 1 are referenced as SEQ ID NOS:1–15.

(LTL), or an unselected decapeptide phage library mix (unamplified phage), were incubated on NG2Δ3-coated or BSA-coated microtiter wells and bound phage quantified. The results shown in FIG. 1 are representative of three independent experiments, and error bars show standard error of the mean (S.E.M.) from triplicate platings. All differences are statistically highly significant as assessed by the student t test ($p<0.01$).

As shown in FIG. 1, both TAASGVRSMH-phage and LTLRWVGLMS-phage specifically bind to NG2. An equivalent number of control phage from the unselected decapeptide phage library showed negligible binding to NG2. Phage containing no peptide inserts also showed negligible binding to NG2. Moreover, binding of the

TABLE 1

Selection of NG2-binding Phage from a Linear Decapeptide Phage Library

| III | IV | V |
|---|---|---|
| TAASGVRSMH | TAASGVRSMH (16) | TAASGVRSMH (SEQ ID NO: 1) (8) |
| LTLRWVGLMS | LTLRWVGLMS (10) | LTLRWVGLMS (SEQ ID NO: 2) (7) |
| GGGTRAGMKY (SEQ ID NO: 3) (2) | | |
| WGKIEDPLRA (SEQ ID NO: 4) | | |
| AGQTLTASGD (SEQ ID NO: 5) | | |
| DLLAVSWLRA (SEQ ID NO: 6) | | |
| SAERGVVAMS (SEQ ID NO: 7) | | |
| AIHSELMWVS (SEQ ID NO: 8) | | |
| FWTERAGWAY (SEQ ID NO: 9) | | |
| MVWSKGPLFL (SEQ ID NO: 10) | | |
| AGTRMSWEVL (SEQ ID NO: 11) | | |
| VSRSSRWGSI (SEQ ID NO: 12) | | |
| DAHVLVPRTP (SEQ ID NO: 13) | | |
| AQGIVLQLAL (SEQ ID NO: 14) | | |
| LSPLLSPATA (SEQ ID NO: 15) | | |

The results shown in Table 1 indicate that two decapeptide sequences, TAASGVRSMH (SEQ ID NO:1) and LTLRWVGLMS (SEQ ID NO:2), were specifically enriched in later rounds of in vitro panning. These sequences first appeared in round II and III and became the exclusive motifs bound to NG2 in the subsequent rounds of selection.

The sequences TAASGVRSMH (SEQ ID NO:1) and LTLRWVGLMS (SEQ ID NO:2) are clearly different, but do have small areas of similarity, VR versus LR, SM versus MS, and ASG versus LTL in TAASGVRSMH (SEQ ID NO:1) and LTLRWVGLMS (SEQ ID NO:2), respectively. Comparison of the sequences to known sequences in data bases revealed no significant similarities between TAASGVRSMH (SEQ ID NO:1) or LTLRWVGLMS (SEQ ID NO:2) and known ligands for NG2/HM proteoglycan (Burg et al., supra, 1998; Burg et al., supra, 1996; Tillet et al., supra, 1997).

These results demonstrate that phage displaying the peptides TAASGVRSMH (SEQ ID NO:1) and LTLRWVGLMS (SEQ ID NO:2) bind to NG2 proteoglycan.

EXAMPLE II

Binding Characteristics of NG2 Binding Phage

This example describes the binding characteristics of phage displaying the peptides TAASGVRSMH (SEQ ID NO:1) and LTLRWVGLMS (SEQ ID NO:2).

Phage displaying TAASGVRSMH (SEQ ID NO:1) or LTLRWVGLMS (SEQ ID NO:2) were tested individually for their ability to bind to NG2Δ3-coated wells. Purified TAASGVRSMH-phage (TAA) and LTLRWVGLMS-phage TAASGVRSMH-phage and LTLRWVGLMS-phage to BSA was minimal compared to binding to NG2.

Figure 2:
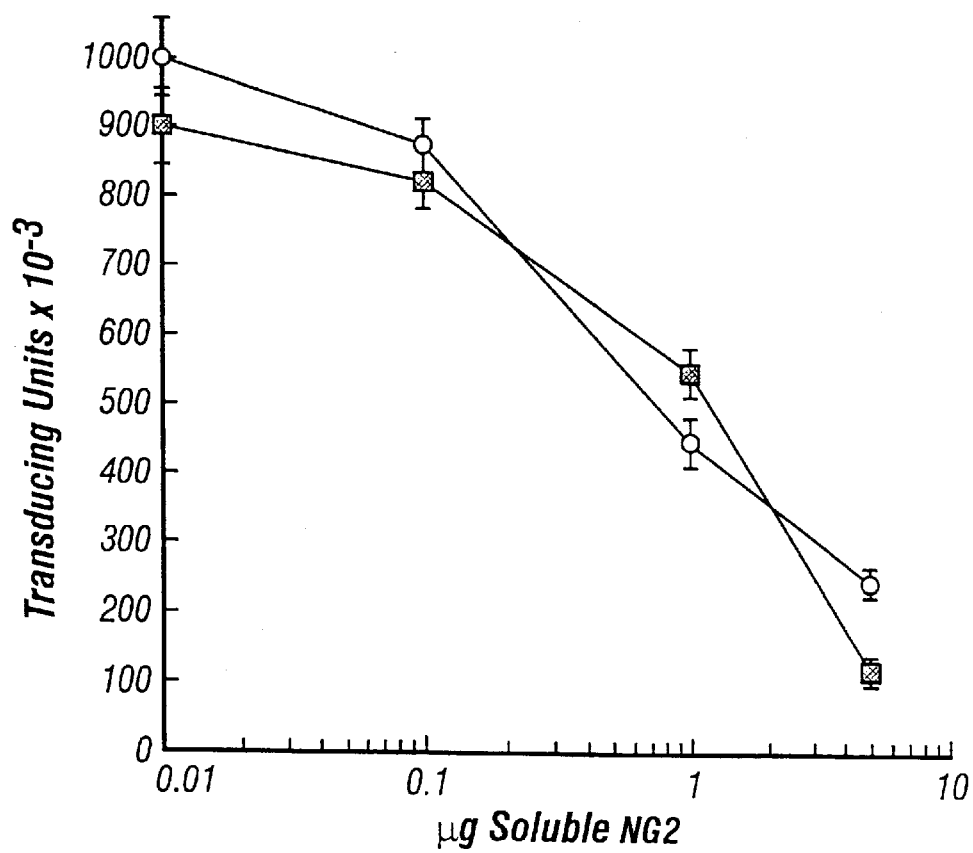
FIG. 2 shows the inhibition of phage binding by soluble NG2. Purified TAASGVRSMH-phage (open circles) and LTLRWVGLMS-phage (closed squares) were incubated in NG2Δ3-coated wells in the presence of the indicated concentrations of soluble NG2Δ3 (NG2), and bound phage were quantified.

To confirm the specificity of these interactions, both species of NG2-binding phage were incubated with increasing concentrations of soluble recombinant NG2Δ3 prior to incubation with NG2Δ3-coated wells. Purified TAASGVRSMH-phage and LTLRWVGLMS-phage were incubated in NG2Δ3-coated wells in the presence of increasing concentrations of soluble NG2Δ3 (NG2). Bound phage were quantified, and the results shown in FIG. 2 are representative of three independent experiments. Error bars show S.E.M. of the mean from triplicate platings of duplicate wells.

As shown in FIG. 2, increasing concentrations of soluble NG2Δ3 resulted in a dose-dependent inhibition of binding of both TAASGVRSMH-phage and LTLRWVGLMS-phage populations to the NG2-coated substratum. Incubation of control phage with increasing concentrations of soluble NG2 had no effect on binding.

These results demonstrate that phage displaying the peptide TAASGVRSMH (SEQ ID NO:1) or LTLRWVGLMS (SEQ ID NO:2) interact specifically with NG2.

EXAMPLE III

Binding of GST-peptide Fusions to NG2

This example shows NG2 binding of GST-peptide fusion proteins containing TAASGVRSMH (SEQ ID NO:1) or LTLRWVGLMS (SEQ ID NO:2).

GST-fusion proteins containing the decapeptide inserts were constructed as previously described (Rajotte et al., J.

Clin. Invest. 102:430–437 (1998)). Briefly, peptide inserts were amplified by polymerase chain reaction (PCR) from the phage using specific M13 primers. PCR products were then digested with BamHI and EcoRI and inserted into the pGEX2TK vector. Fusion proteins were produced and purified according to the manufacturer's instructions (Pharmacia Biotech Inc.; Piscataway N.J.).

Solid-phase assays were performed as described previously (Burg et al., supra, 1996). Briefly, fusion proteins (2 µg/well) were coated onto microtiter wells overnight at 4° C. Wells were blocked with 2% BSA in PBS and incubated with soluble NG2Δ3 (1 µg/well) for 2 hr at room temperature. After washing, wells were then incubated with an anti-NG2 polyclonal antibody followed by washing and incubation with an $^{125}$I-labeled goat anti-rabbit IgG. After final washing, bound radioactivity was determined using a gamma counter. For competition studies, soluble NG2Δ3 was preincubated 15 min with increasing concentrations of soluble GST-fusion proteins prior to incubation on wells coated with GST-fusion protein.

GST-peptide fusion proteins containing one of the two NG2-binding motifs, TAASGVRSMH (SEQ ID NO:1) or LTLRWVGLMS (SEQ ID NO:2), were tested for their ability to inhibit binding of phage to NG2Δ3-coated wells. Purified TAASGVRSMH-phage and LTLRWVGLMS-phage were incubated in NG2Δ3-coated wells in the presence of increasing concentrations of GST-TAASGVRSMH fusion protein, GST-LTLRWVGLMS fusion protein, or GST alone, and phage binding was quantified. Results shown in FIG. 3 are representative of three independent experiments and error bars show S.E.M. of the mean from triplicate platings of duplicate wells. The differences indicated by "*" are considered highly significant by student t test (p<0.01).

Figure 3A:
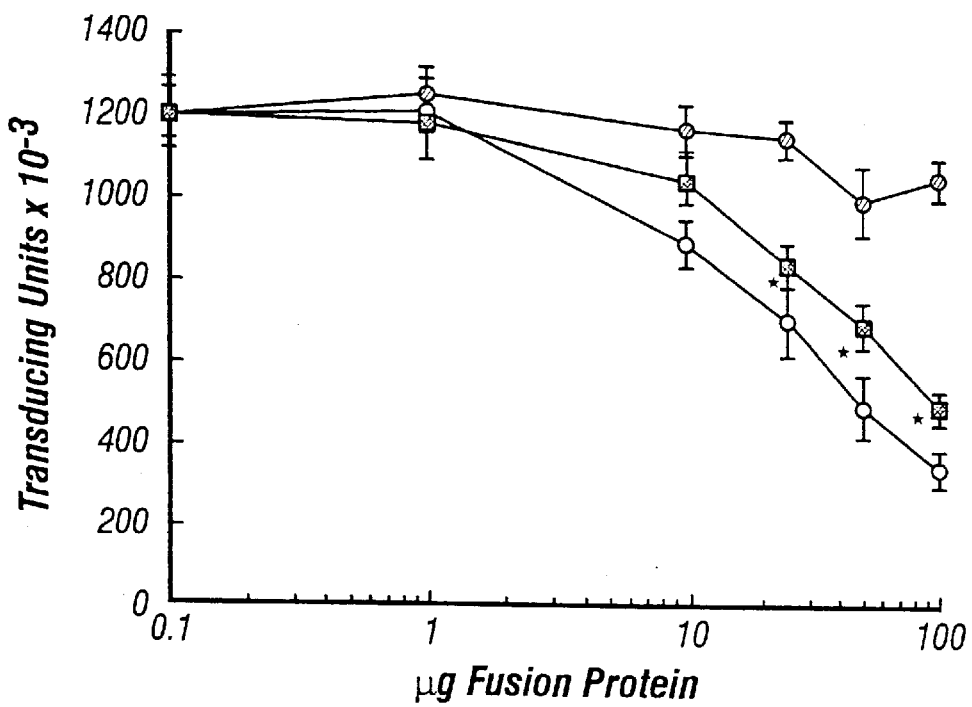
FIG. 3 shows inhibition of phage binding by cognate peptide sequences. Purified TAASGVRSMH-phage (panel A) and LTLRWVGLMS-phage (panel B) were incubated in NG2Δ3-coated wells in the presence of the indicated concentrations of GST-TAASGVRSMH fusion protein (open circles), GST-LTLRWVGLMS fusion protein (stippled squares), or GST alone (closed circles), and phage binding was quantified.

As shown in FIG. 3, when TAASGVRSMH-phage were allowed to bind to NG2 coated wells in the presence of increasing concentrations of the cognate fusion protein, GST-TAASGVRSMH, a dose-dependent decrease in binding was observed (FIG. 3A). The binding of TAASGVRSMH-phage to NG2 was also inhibited by increasing concentrations of GST-LTLRWVGLMS. In contrast, incubation of the phage with a control GST protein containing no peptide insert had little effect on binding.

Figure 3B:
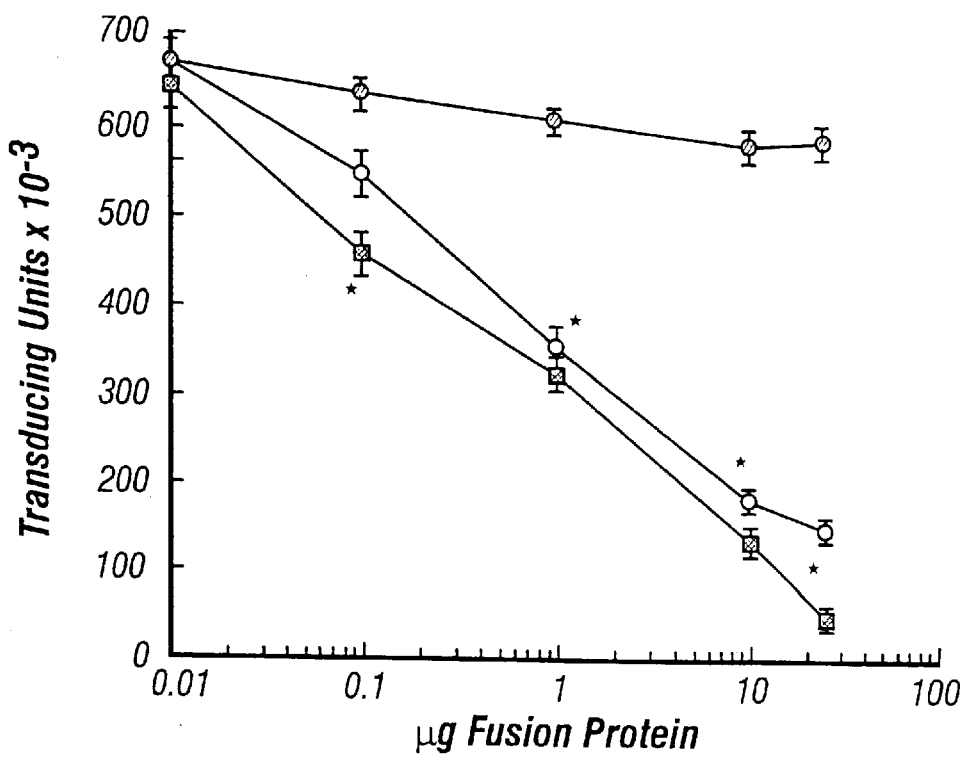

A similar result was obtained when binding of LTLRWVGLMS-phage was tested in the presence of increasing concentrations of GST fusion proteins. Both GST-TAASGVRSMH and GST-LTLRWVGLMS fusion proteins inhibited the binding of LTLRWVGLMS-phage to NG2, whereas the control GST protein had no significant effect on the binding (FIG. 3B).

The ability of soluble NG2 to bind to GST-TAASGVRSMH and GST-LTLRWVGLMS was tested by using a solid phase assay. Purified NG2Δ3 was incubated in wells coated with GST-TAASGVRSMH or GST-LTLRWVGLMS in the absence of inhibitor, or after preincubation with 50 mg of soluble GST-TAASGVRSMH, GST-LTLRWVGLMS or GST alone. Binding of NG2Δ3 was determined, and the results shown in FIG. 4 are representative of three independent experiments. Error bars show S.E.M. of the mean from triplicate wells. The differences indicated by "*" are considered significant by student t test (p<0.05). The differences indicated by "**" are considered highly significant by student t test (p<0.01).

Figure 4A:
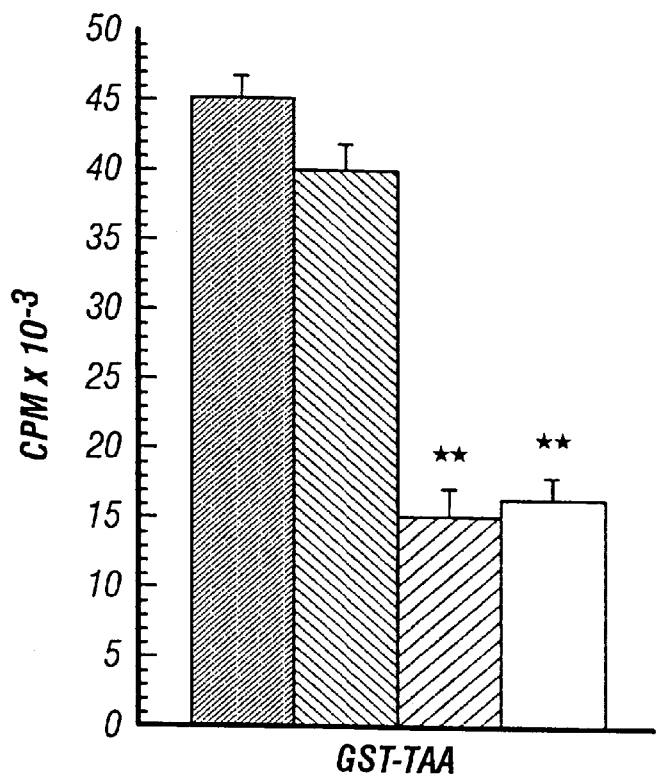
FIG. 4 shows binding of NG2 to immobilized GST-peptide fusion proteins. Purified NG2Δ3 was incubated in wells coated with GST-TAASGVRSMH (Panel A; GST-TAA) or GST-LTLRWVGLMS (Panel B; GST-LTL) in the absence of inhibitor (solid bar), or after preincubation with 50 mg of soluble GST-TAASGVRSMH (hatched bar), GST-LTLRWVGLMS (open bar) or GST alone (stippled bar). Binding of NG2Δ3 was determined.
Figure 4B:
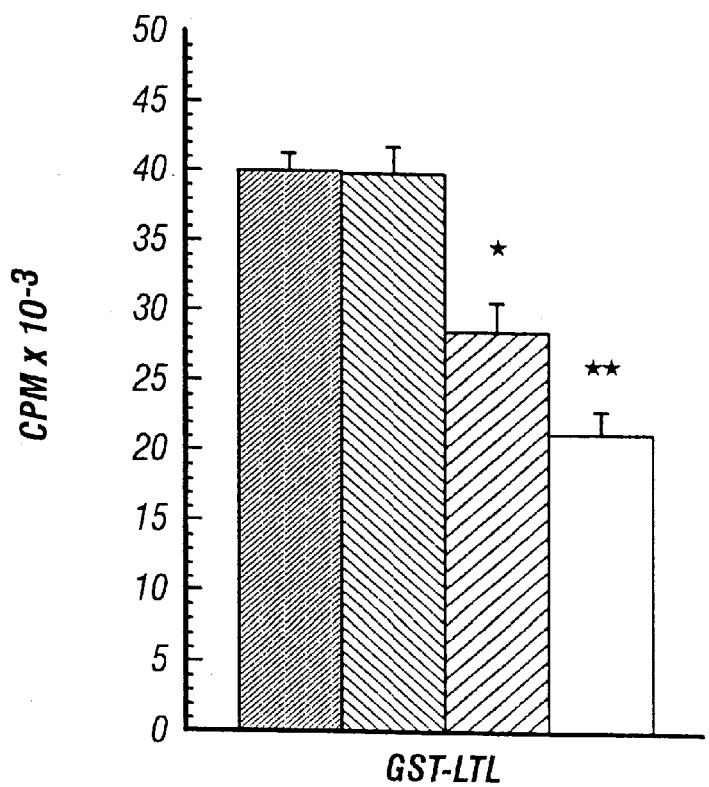

Soluble NG2 was found to bind much more effectively to the immobilized fusion proteins than to GST alone. In addition, preincubation of NG2 with increasing concentrations of GST-TAASGVRSMH resulted in a dose-dependent decrease in binding of NG2 to wells coated with this same fusion protein (FIG. 4A). Preincubation of NG2 with increasing concentrations of GST-LTLRWVGLMS also inhibited binding of NG2 to wells coated with GST-TAASGVRSMH. These results indicate that the two peptides bind to similar sites on NG2. Both of the soluble fusion proteins also inhibited the binding of NG2 to wells coated with GST-LTLRWVGLMS (FIG. 4B).

These results demonstrate that peptides TAASGVRSMH (SEQ ID NO:1) and LTLRWVGLMS (SEQ ID NO:2) specifically bind to NG2.

EXAMPLE IV

Phage Expressing NG2 Binding Peptides Target Tumors In Vivo

This example shows that phage expressing peptides that bind to NG2 can target tumors in vivo.

In vivo phage targeting was performed on 4–6 week old NG2 knockout mice and control F1 wild-type mice. NG2 knockout mice were generated using embryonic stem cell technology. Briefly, an adult Balb/c mouse liver genomic library in the EMBL-3 vector (ML1009d, Clontech; Palo Alto Calif.) was grown in LE392 host cells. $10^6$ phage plaques from the library were screened on nitrocellulose using a 1.42 kb rat NG2 cDNA probe representing NG2 bases 882–2301 (Nishiyama et al., supra, 1991a). This DNA segment was excised from the full length rat NG2 cDNA by digestion with KpnI, isolated by agarose (1%) gel electrophoresis, and labeled with ($^{32}$P)dCTP using a random primer oligolabeling kit (Pharmacia)(Nishiyama and Stallcup, supra, 1993).

Two overlapping clones from the 5' end of the NG2 gene were isolated from the mouse genomic library and analyzed by partial sequencing and restriction mapping. The more 5' of the two clones, a 17.2 kb segment designated K2, was selected for further use. K2 did not contain the coding region for the NG2 signal peptide, but contained a 162 bp exon coding for the initial segment of the mature NG2 peptide and a 603 bp exon coding for the adjacent segment of the polypeptide. Subsequent cloning results revealed that the signal peptide was encoded by an additional exon, which were designated as exons 2 and 3 for the 162 and 603 bp segments, respectively. A 6.1 kb segment containing both exons 2 and 3 was excised from the K2 clone and ligated into the Bluescript (SK⁻) vector (Stratagene; San Diego Calif.). This construct was designated pBX6.

The targeting vector was constructed using homologous recombination (Mansour et al., Nature 336:348–352 (1988); Capecchi, Science 244:1288–1292 (1989)). To disrupt the NG2 coding sequence and to allow positive selection of targeted ES cell clones, a 1.1 kb neo fragment containing the TK promoter and polyadenylation signal was excised from the pMClneopA vector (Stratagene) and inserted into the EcoRI site in NG2 exon 3. This pBX6neopA vector was further modified to allow for negative selection using the 0.84 kb DT-A gene (diphtheria toxin A) excised from plasmid pMC1DT-A (a gift from Dr. S. Aizawa, Kumamoto University). DT-A was inserted at the 3' end of the construct to yield the final targeting vector, designated as pBX6neopADT-A.

Following linearization with NotI, the targeting vector was electroporated into the R1 ES cell line. For embryonic stem cell manipulation, the R1 line of embryonic stem cells (Nagy et al., Proc. Natl. Acad. Sci. USA 90:8424–8428 (1993)) was maintained in culture according to the method of Wurst and Joyner (in *Gene Targeting*, Joyner, ed., pp.33–61, IRL Press, Oxford (1995)).

After selection in 300 μg/ml G418, more than 100 neomycin-resistant ES cell colonies were obtained. Forty of these were analyzed for correct NG2 targeting by Southern blotting of SacI and BamHI digests of ES cell genomic DNA. Briefly, for Southern blots, high molecular mass genomic DNA from embryonic stem (ES) cells or from mouse tail was prepared as described previously (Blin and Stafford, *Nucl. Acids Res.* 3:2303–2308 (1976)). SacI and BamHI digests were fractionated by agarose (0.7%) gel electrophoresis and transferred to nitrocellulose according to the method of Southern (*J. Mol. Biol.* 98:503–517 (1975)). Blots were probed with a $^{32}$P-labeled, 603 bp PCR product (M2/MIII) representing NG2 exon 3.

In SacI and BamHI digests of wild type ES cell DNA, the M2/MIII probe should hybridize with 5.5 kb and 9.0 kb restriction fragments, respectively. Since for both of these enzymes the 3' restriction sites lie outside the NG2 targeting construct, production of appropriately-sized fragments from targeted DNA can only occur when the targeting construct is integrated into the correct site in the genome. Thus, in correctly targeted ES cells containing the 1.1 kb neo insert, SacI digestion should yield a 6.6 kb fragment that hybridizes with M2/MIII. Due to the presence of the additional BamHI site in the neo insert, BamHI digestion should yield hybridizing fragments of 1.8 and 8.3 kb. However, only the 8.3 kb fragment is indicative of correct targeting since the 1.8 kb segment is contained wholly within the targeting construct itself and, thus, is independent of the location of the targeting construct in the genome. Six ES cell clones were identified which satisfied these two sets of requirements. Three of these clones were chosen for further studies on the basis of their normal number of chromosomes.

To generate targeted mice, ES cell clones 9.7, 6.5 and 2.5 were injected into C57B1/6 blastocysts, which were then transferred to CD-1 recipient females. Targeted R1 cells derived from the mouse strain (129/SVx129/SV-CP) F1 were injected into day 3.5 C57B1/6 embryos and subsequently transferred to CD-1 recipient females as described previously (Hogan et al., *Manipulating the Mouse Embryo*, Cold Spring Harbor Press (1994)). Offspring identified as being chimeric on the basis of coat color were mated to C57B1/Swiss partners to produce mice that were heterozygous for the targeted NG2 gene. Three of the chimeric mice (one derived from ES cell clone 2.5 and two derived from clone 9.7) were found to be capable of producing heterozygous offspring. Heterozygotes were identified by Southern blotting of SacI digested tail DNA using the M2/MIII probe. NG2$^{+/-}$ heterozygotes were then crossed to obtain mice that were homozygous for the targeted NG2 allele (NG2$^{-/-}$). Offspring from these matings were analyzed not only by Southern blotting to identify the NG2$^{-/-}$ genotype, but also by immunoblotting to detect the presence of the NG2 polypeptide itself. Southern blotting and immunoblotting were performed on one litter of postnatal day 4 mice resulting from a heterozygote cross. The Southern blot data established that the litter included four wild type, four heterozygous, and two homozygous targeted mice.

For immunological detection of NG2, NG2 polyclonal and monoclonal antibodies that were previously described were used (Stallcup et al., *J. Cell Biol.* 111:3177–3188 (1990); Nishiyama et al., supra, 1991a). For immunoblotting, proteins were electrophoretically transferred from sodium dodecyl sulfate-polyacrylamide gel electrophoresis (SDS-PAGE) gels to IMMOBILON P membranes (Millipore; Bedford MA) using a pH 11 CAPS (3-(cyclohexylamino)-1-propanesulfonic acid) buffer system. After overnight blocking in 20 mM Tris-HCl, 0.5 M NaCl, pH 7.4, containing 10% BSA and 5% newborn calf serum, membranes were incubated with appropriate first antibodies for two hours. After washing with Tris buffered saline, detection was accomplished using horse radish peroxidase (HRP) labeled second antibodies (BioRad; Hercules Calif.), an enhanced chemiluminescence (ECL) kit (Amersham; Arlington Heights Ill.), and Kodak BIOMAX MR film (Eastman Kodak Co.; Rochester N.Y.). From immunoblotting analysis, the two NG2$^{-/-}$ offspring were determined to lack immunoreactive NG2, while wild type offspring had the highest levels of NG2. Heterozygous offspring had intermediate levels of NG2.

For immunocytochemistry of optic nerve, 20 μm cryostat sections of 2% paraformaldehyde-fixed optic nerve were immunostained for NG2 and laminin as described previously. Rabbit antibody against human laminin was a gift from Dr. Eva Engvall (The Burnham Institute; San Diego Calif.). All specimens were coverslipped in Immumount (Shandon; Pittsburgh Pa.) and examined by epifluorescence using a Nikon Optiphot microscope (Nikon; Melville N.Y.) equipped with fluorescein, rhodamine and phase-contrast optics. Immunohistochemical analysis of optic nerve sections from wild type and knockout mice revealed the presence of both NG2 positive capillaries and oligodendrocyte progenitor cells in the wild type tissue, but not in tissue from the null animals.

Four lines of mice were propagated from the initial crosses between NG2$^{+/-}$ heterozygotes: (1) NG2$^{-/-}$ homozygotes derived from ES clone 2.5, (2) two lines of NG2$^{-/-}$ homozygotes derived from ES cell clone 9.7, and (3) NG2$^{+/+}$ homozygotes with the same genetic background as the two lines of knockout mice (designated as F1 wild type). On a gross level, the NG2 knockout mice did not exhibit an obvious mutant phenotype. Litter sizes, birth weights, postnatal development, ability to breed, and life spans all appeared comparable to those of the F1 wild type mice. Organogenesis also appeared to occur normally in the knockout mice, as judged by comparison of hematoxylin and eosin stained sections from F1 wild type and NG2 null embryos at various stages of development.

To verify that NG2 is not expressed in tissues of the knockout mouse, immunofluorescence was used to compare primary cultures of aortic smooth muscle cells from postnatal day 1 wild type mice and NG2 null mice. Briefly, living aortic smooth muscle cells were used for detection of NG2 and von Willebrand factor by indirect immunofluorescence (Stallcup et al., supra, 1990; Nishiyama et al., *Development* 111:933–944 (1991b)). For detection of μ-smooth muscle actin and bromodeoxyuridine, cells were first fixed in methanol or methanol containing 5% acetic acid, respectively, at −20° C. for 10 min. Monoclonal anti-α smooth muscle actin was obtained from Sigma (St. Louis Mo.). Rabbit anti-von Willebrand factor antibody was purchased from Dako (Carpinteria Calif.). Monoclonal antibody against bromodeoxyuridine (clone BU-1) was obtained from Amersham.

Wild type cells expressed high levels of NG2 and, consistent with the expected phenotype of smooth muscle, the cells expressed α-smooth muscle actin but not von Willebrand factor, an endothelial cell marker. In contrast, cells derived from NG2$^{-/-}$ pups were positive for α-smooth muscle actin but did not exhibit NG2 expression. The NG2 null cells also did not express von Willebrand factor. Tissue sections of aortas from both wild type and knockout mice exhibit similar gross morphologies, but can be distinguished in immunohistochemical tests by the absence of NG2 on the smooth muscle cells of the NG2 null specimens.

For tumor generation, B16F10 mouse melanoma cells were harvested from subconfluent cultures using non-enzymatic cell dissociation buffer (GIBCO; Life Technologies Inc.; Gaithersburg Md.). Cells ($1 \times 10^6$ cells in 0.2 ml Dulbecco Modified Eagles Medium (DMEM)) were injected subcutaneously into the mouse right flank of NG2 knockout mice or control F1 wild type mice. Tumors were monitored between 10 to 20 days post-injection, and animals bearing tumors approximately 1–2 cm in diameter were selected for phage targeting.

Tumor targeting using phage was performed as previously described (Pasqualini et al., *Nature Biotechnol.* 15:542–546 (1997)). Briefly, phage ($1 \times 10^9$ to $1 \times 10^{10}$), either RGD-4C-phage, TAASGVRSMH-phage, LTLRWVGLMS-phage, or phage of an unselected library mix (unamplified decapeptide library) were injected intravenously (lateral tail vein) into mice anesthetized with 0.017 ml Avertin per g and allowed to circulate for 5 min. Mice were then perfused through the heart with 5 ml of DMEM. Tumors and brains were removed and weighed. Tissues were homogenized in DMEM containing protease inhibitors (Pasqualini and Ruoslahti, *Nature* 380:364–466 (1996)), and phage were rescued and quantified from these tissues as described previously (Pasqualini and Ruoslahti, supra, 1996; Pasqualini et al., supra, 1997).

To determine whether NG2-binding phage were capable of targeting NG2 within tumor vasculature, the ability of NG2 binding phage to home to the vasculature of B16 melanoma xenografts growing in either wild-type or NG2 null mice was determined. Tumor B16F10 was introduced into NG2-null mice or F1 wild-type mice as described above, and the tumor-bearing mice were injected intravenously via the tail vein with $10^{10}$ TU of purified TAASGVRSMH-phage, LTLRWVGLMS-phage, RGD-4C-phage, or unselected library mix of phage. Mice were perfused and phage were recovered from tumors and from brain. The phage yields were quantified as the number of transducing units recovered per gram of tissue. The results shown in FIG. 5 are expressed as a ratio of tumor homing phage to brain homing phage and are representative of three independent experiments. Error bars show S.E.M. of the mean from triplicate platings. All differences in panel A of FIG. 5 considered highly significant by student t test ($p < 0.01$).

Figure 5A:
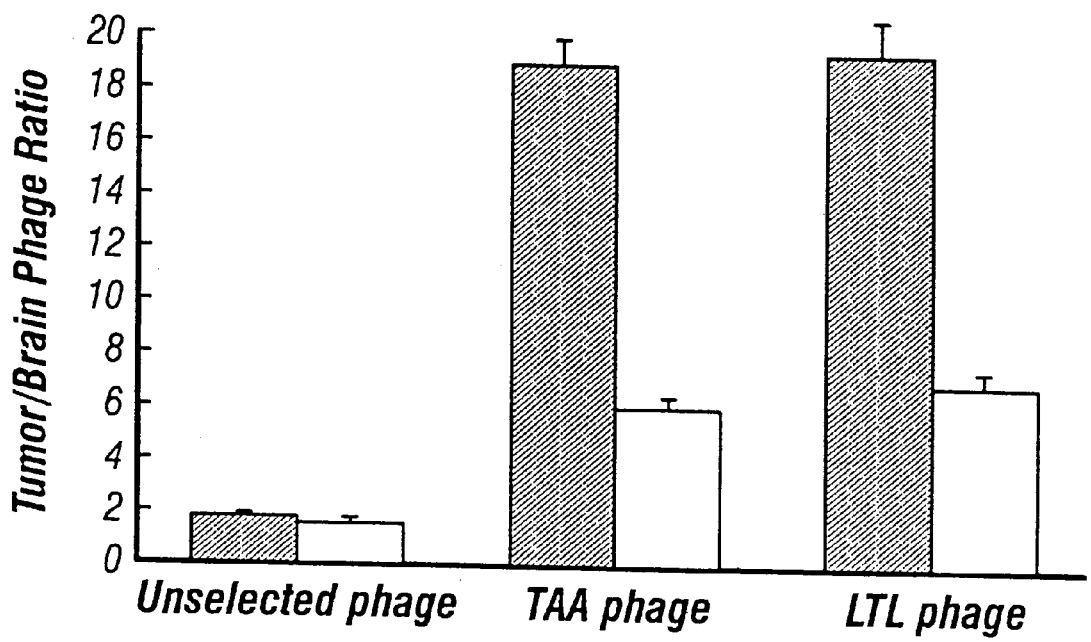
FIG. 5 shows homing of phage to tumor vasculature. Tumor B16F10 was introduced into NG2-null mice (gray bars) or F1 wild-type mice (solid bars), and the tumor-bearing mice were injected intravenously via the tail vein with $10^{10}$ TU of purified TAASGVRSMH-phage (TAA phage; panel A), LTLRWVGLMS-phage (LTL phage; panel A), RGD-4C-phage (panel B), or unselected library mix of phage (unselected phage) (panels A and B). Mice were perfused, and phage were recovered from tumors and from brain. The phage yields were quantified as the number of transducing units recovered per gram of tissue.
Figure 5B:
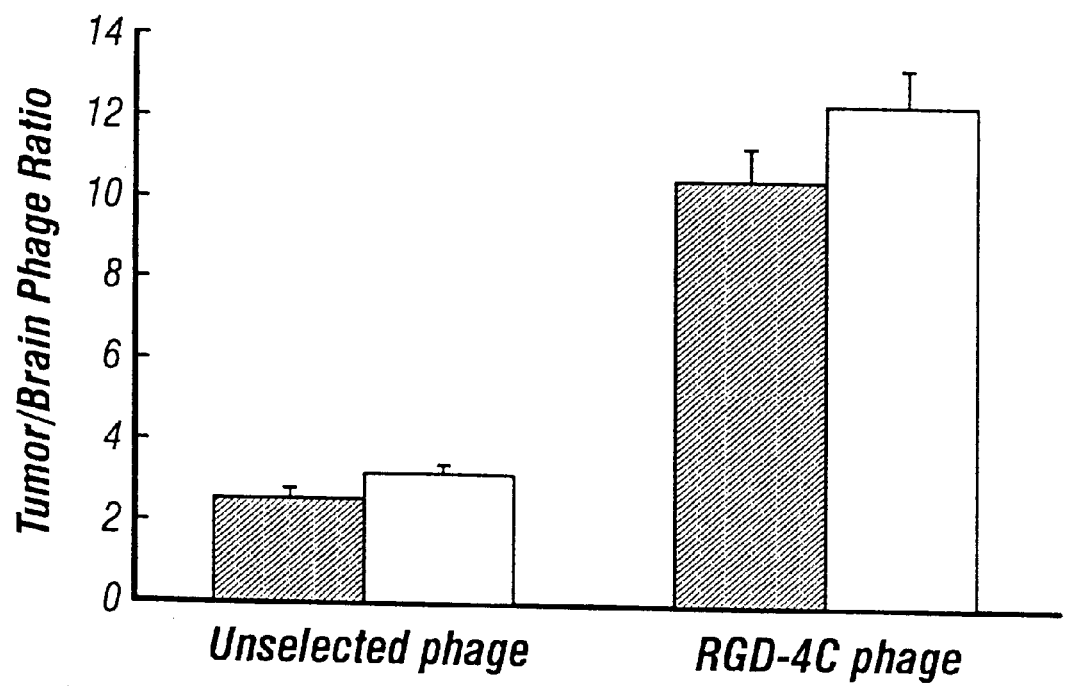

When an equivalent number of NG2-binding phage were injected intravenously into the two lines of tumor-bearing mice, both TAASGVRSMH-phage and LTLRWVGLMS-phage were found to home specifically to tumors of wild-type mice expressing NG2. In contrast, there was much less homing to tumors established in NG2 null mice (FIG. 5A). In addition, control phage did not show selective accumulation to the tumors established in either wild-type or NG2 knock-out mice. In a separate experiment, tumor-targeting phage previously shown to bind to $\alpha_v$ integrins exhibited equivalent abilities to target tumors in wild type and NG2 null mice (FIG. 5B) (Pasqualini et al., supra, 1997). This result indicates that, since phage did not target to NG2 null mice, the homing of NG2-binding phage to tumors in wild-type mice is mediated by NG2 expression and is not due to other differences between tumor vasculature of wild-type and NG2 null mice.

For immunohistochemistry, B16F10 tumors were grown in NG2-knockout and F1 control mice as described above. Tumors were removed, fresh frozen, and 25 μm sections cut on a cryostat. Tumor vascularization was visualized using a mixture of a rat anti-mouse CD31 monoclonal antibody (Pharmacia Biotech) and anti-NG2 polyclonal antibodies. Secondary staining was performed with fluorescein isothiocyanate (FITC)-conjugated anti-rabbit immunoglobulin and rhodamine isothiocyanate (RITC)-conjugated anti-rat immunoglobulin antibodies (Biosource International; Camarillo Calif.). Confocal images through a single section were obtained using a Zeiss LSM 410 laser scanning confocal microscope (Carl Zeiss; Thornwood N.Y.). Superimposition of confocal images revealed NG2 expression on pericytic cells abluminally apposed to CD31-positive endothelial cells in wild-type mice. No NG2 expression was observed in the tumor vasculature of the NG2 knockout mouse. B16 cells are NG2 and CD31-negative and do not contribute to the staining pattern.

Immunohistochemical examination of the tumor vasculature in wild-type mice showed NG2 expression was limited to vascular pericytes, which were abluminally-associated with CD31-positive endothelial cells. The abluminally-associated pericytes are located on the side of endothelial cells away from the lumen of the vessel and form the layer outside the endothelial cells, which line the vessel lumen. NG2-knockout mice exhibited no NG2 immunoreactivity but showed normal CD31-positive endothelial cell staining. No other major difference between vasculature of B16 tumors grown in wild-type and NG2-knockout mice was observed. Furthermore, even though phage are relatively large particles and are not likely to be able to penetrate an intact endothelial layer in the short duration of the in vivo homing experiment, these results also indicate that pericytes in tumor vessels are accessible to circulating probes such as the angiogenic vasculature homing molecules TAASGVRSMH (SEQ ID NO:1) and LTLRWVGLMS (SEQ ID NO:2) linked to a relatively large moiety such as phage.

These results demonstrate that phage bearing peptides that bind to NG2, in particular TAASGVRSMH (SEQ ID NO:1) and LTLRWVGLMS (SEQ ID NO:2), home to tumor vasculature in vivo.

All journal article, reference, and patent citations provided above, in parentheses or otherwise, whether previously stated or not, are incorporated herein by reference.

Although the invention has been described with reference to the examples above, it should be understood that various modifications can be made without departing from the spirit of the invention. Accordingly, the invention is limited only by the following claims.

What is claimed is:

1. A peptide comprising the amino acid sequence TAASGVRSMH (SEQ ID NO:1).

2. A peptide comprising the amino acid sequence LTLRWVGLMS (SEQ ID NO:2).

3. A conjugate comprising a peptide linked to a moiety, wherein said peptide is selected from the group consisting of TAASGVRSMH (SEQ ID NO:1) and LTLRWVGLMS (SEQ ID NO:2).

4. The conjugate of claim 3, wherein said moiety is a cytotoxic agent.

5. The conjugate of claim 3, wherein said moiety is a drug.

6. The conjugate of claim 3, wherein said moiety is a cancer chemotherapeutic agent.

7. The conjugate of claim 6, wherein said cancer chemotherapeutic agent is doxorubicin.

8. The conjugate of claim 3, wherein said moiety is a detectable moiety.

9. The conjugate of claim 3, wherein said moiety is selected from the group consisting of, a liposome, a cell and a virus.

10. The conjugate of claim 3, wherein said moiety is a grafted polypeptide.

11. A method of targeting a moiety to angiogenic vasculature in a tumor in vivo, comprising contacting said angiogenic vasculature with an angiogenic vasculature homing molecule linked to a moiety that selectively homes to a NG2/HM proteoglycan, thereby targeting angiogenic vasculature expressing NG2/HM proteglycan, wherein said angiogenic vasculature homing molecule is not an antibody and wherein said molecule is selected from the group of peptides consisting of TAASGVRSMH (SEQ ID NO:1) and LTLRWVGLM$ (SEQ ID NO:2).

12. The method of claim 11, wherein said moiety is a cytotoxic agent.

13. The method of claim 11, wherein said moiety is a drug.

14. The method of claim 11, wherein said moiety is a cancer chemotherapeutic agent.

15. The method of claim 14, wherein said cancer chemotherapeutic agent is doxorubicin.

16. The method of claim 11, wherein said moiety is a detectable moiety.

17. The method of claim 11, wherein said moiety is selected from the group consisting of a liposome, a cell and a virus.

18. The method of claim 11, wherein said moiety is a grafted polypeptide.

19. A method of inhibiting angiogenesis in a tumor of a subject, comprising administering to the subject a conjugate comprising a moiety that inhibits angiogenesis linked to an angiogenic vasculature homing molecule that selectively binds a NG2/HM proteoglycan, whereby said moiety inhibits angiogenesis in angiogenic vasculature expressing NG2/HM proteoglycan, wherein said angiogenic vasculature homing molecule is not an antibody and wherein said molecule is selected from the group of peptides consisting of TAASGVRSMH (SEQ ID NO:1) and LTLRWVGLMS (SEQ ID NO:2).

20. The method of claim 19, wherein said moiety is a cytotoxic agent.

21. The method of claim 19, wherein said moiety is a drug.

22. The method of claim 19, wherein said moiety is a cancer chemotherapeutic agent.

23. The method of claim 22, wherein said cancer chemotherapeutic agent is doxorubicin.

24. The method of claim 19, wherein said moiety is selected from the group consisting of a liposome, a cell and a virus.

25. The method of claim 19, wherein said moiety is a grafted polypeptide.

26. A method of targeting a moiety to a tumor in vivo, comprising contacting said tumor with a homing molecule linked to said moiety that selectively homes to a NG2/HM proteoglycan, wherein NG2/HM proteoglycan is expressed in said tumor, thereby targeting said tumor, wherein said homing molecule is not an antibody and wherein said homing molecule is selected from the group of peptides consisting of TAASGVRSMH (SEQ ID NO:1) and LTLRWVGLMS (SEQ ID NO:2).

27. The method of claim 26, wherein said moiety is a cytotoxic agent.

28. The method of claim 26, wherein said moiety is a drug.

29. The method of claim 26, wherein said moiety is a cancer chemotherapeutic agent.

30. The method of claim 29, wherein said cancer chemotherapeutic agent is doxorubicin.

31. The method of claim 26, wherein said moiety is a detectable moiety.

32. The method of claim 26, wherein said moiety is selected from the group consisting of a liposome, a cell and a virus.

33. The method of claim 26, wherein said moiety is a grafted polypeptide.

* * * * *

UNITED STATES PATENT AND TRADEMARK OFFICE
CERTIFICATE OF CORRECTION

PATENT NO. : 6,528,481 B1
DATED : March 4, 2003
INVENTOR(S) : Burg et al.

It is certified that error appears in the above-identified patent and that said Letters Patent is hereby corrected as shown below:

Column 41,
Line 8, please delete "$" and replace therefore with -- S --.

Signed and Sealed this

Thirteenth Day of July, 2004

JON W. DUDAS
*Acting Director of the United States Patent and Trademark Office*

SEQUENCE LISTING

<160> NUMBER OF SEQ ID NOS: 16

<210> SEQ ID NO 1
<211> LENGTH: 10

```
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1

Thr Ala Ala Ser Gly Val Arg Ser Met His
 1               5                  10

<210> SEQ ID NO 2
<211> LENGTH: 10
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 2

Leu Thr Leu Arg Trp Val Gly Leu Met Ser
 1               5                  10

<210> SEQ ID NO 3
<211> LENGTH: 10
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 3

Gly Gly Gly Thr Arg Ala Gly Met Lys Tyr
 1               5                  10

<210> SEQ ID NO 4
<211> LENGTH: 10
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 4

Trp Gly Lys Ile Glu Asp Pro Leu Arg Ala
 1               5                  10

<210> SEQ ID NO 5
<211> LENGTH: 10
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 5

Ala Gly Gln Thr Leu Thr Ala Ser Gly Asp
 1               5                  10

<210> SEQ ID NO 6
<211> LENGTH: 10
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 6

Asp Leu Leu Ala Val Ser Trp Leu Arg Ala
```

```
<210> SEQ ID NO 7
<211> LENGTH: 10
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 7

Ser Ala Glu Arg Gly Val Val Ala Met Ser
 1               5                  10

<210> SEQ ID NO 8
<211> LENGTH: 10
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 8

Ala Ile His Ser Glu Leu Met Trp Val Ser
 1               5                  10

<210> SEQ ID NO 9
<211> LENGTH: 10
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 9

Phe Trp Thr Glu Arg Ala Gly Trp Ala Tyr
 1               5                  10

<210> SEQ ID NO 10
<211> LENGTH: 10
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 10

Met Val Trp Ser Lys Gly Pro Leu Phe Leu
 1               5                  10

<210> SEQ ID NO 11
<211> LENGTH: 10
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 11

Ala Gly Thr Arg Met Ser Trp Glu Val Leu
 1               5                  10

<210> SEQ ID NO 12
<211> LENGTH: 10
<212> TYPE: PRT
<213> ORGANISM: Artificial Sequence
<220> FEATURE:
<223> OTHER INFORMATION: Description of Artificial Sequence: Synthetic
```

Peptide

<400> SEQUENCE: 12

Val Ser Arg Ser Ser Arg Trp Gly Ser Ile
 1               5                   10

<210> SEQ ID NO 13
<211> LENGTH: 10
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 13

Asp Ala His Val Leu Val Pro Arg Thr Pro
 1               5                   10

<210> SEQ ID NO 14
<211> LENGTH: 10
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 14

Ala Gln Gly Ile Val Leu Gln Leu Ala Leu
 1               5                   10

<210> SEQ ID NO 15
<211> LENGTH: 10
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 15

Leu Ser Pro Leu Leu Ser Pro Ala Thr Ala
 1               5                   10

<210> SEQ ID NO 16
<211> LENGTH: 8
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 16

Cys Leu Ser Gly Ser Leu Ser Cys
 1               5